(12) United States Patent
Delhomel et al.

(10) Patent No.: US 12,391,712 B2
(45) Date of Patent: Aug. 19, 2025

(54) PHOSPHATE DERIVATIVES OF RORGAMMA MODULATORS AND USES THEREOF

(71) Applicant: GENFIT, Loos (FR)

(72) Inventors: Jean-François Delhomel, Arras (FR); Robert Walczak, Lille (FR); Peggy Parroche, Loos (FR); Anne-Marie Saveret, Asnieres-les-Dijon (FR)

(73) Assignee: GENFIT, Loos (FR)

( * ) Notice: Subject to any disclaimer, the term of this patent is extended or adjusted under 35 U.S.C. 154(b) by 670 days.

(21) Appl. No.: 17/786,593

(22) PCT Filed: Dec. 17, 2020

(86) PCT No.: PCT/EP2020/086904
§ 371 (c)(1),
(2) Date: Jun. 17, 2022

(87) PCT Pub. No.: WO2021/123076
PCT Pub. Date: Jun. 24, 2021

(65) Prior Publication Data
US 2023/0039185 A1    Feb. 9, 2023

(30) Foreign Application Priority Data

Dec. 19, 2019   (EP) .................... 19306700

(51) Int. Cl.
| | | |
|---|---|---|
| *C07F 9/6558* | (2006.01) | |
| *A61K 9/00* | (2006.01) | |
| *C07F 9/572* | (2006.01) | |
| *C07F 9/6539* | (2006.01) | |

(52) U.S. Cl.
CPC .......... *C07F 9/65586* (2013.01); *A61K 9/008* (2013.01); *C07F 9/5728* (2013.01); *C07F 9/6539* (2013.01); *C07F 9/65583* (2013.01)

(58) Field of Classification Search
CPC .. C07F 9/6539; C07F 9/5728; C07F 9/65586; C07F 9/65583
See application file for complete search history.

(56) References Cited

U.S. PATENT DOCUMENTS 6,765,014 B1 * 7/2004 Corrie .................. A61P 25/00
514/415

FOREIGN PATENT DOCUMENTS

| WO | WO 2016/196742 | 12/2016 |
|---|---|---|
| WO | WO 2018/138359 | 8/2018 |
| WO | WO 2018/138362 | 8/2018 |
| WO | WO 2019/195159 | 10/2019 |

OTHER PUBLICATIONS

Wermuth, C. G. "Preparation of Water-Soluble Compounds by Covalent Attachment of Solubilizing Moieties" *Wermuth's The Practice of Medicinal Chemistry*, 2008, pp. 1-46, Ch. 38.
Written Opinion in International Application No. PCT/EP2020/086904, Feb. 1, 2021, pp. 1-7.

* cited by examiner

*Primary Examiner* — Laura L Stockton
(74) *Attorney, Agent, or Firm* — SALIWANCHIK, LLOYD & EISENSCHENK

(57) ABSTRACT

The present invention relates to phosphate derivatives of formula (I), and their therapeutic uses, preferably for treating a respiratory disease. The present invention further relates to pharmaceutical compositions and devices comprising such compounds.

14 Claims, 4 Drawing Sheets

PHOSPHATE DERIVATIVES OF RORGAMMA MODULATORS AND USES THEREOF

CROSS-REFERENCE TO RELATED APPLICATION

This application is the U.S. national stage application of International Patent Application No. PCT/EP2020/086904, filed Dec. 17, 2020.

TECHNICAL FIELD OF THE INVENTION

The present invention relates to the field of medicine, in particular phosphate derivatives of RORgamma modulators. It also relates to the pharmaceutical compositions comprising such derivatives, and their use for preventing and/or treating a respiratory disease.

BACKGROUND OF THE INVENTION

Respiratory disorders related to airway inflammation include a number of severe lung diseases including asthma and COPD (Chronic Obstructive Pulmonary Diseases). The airways of asthmatic patients are infiltrated by inflammatory leukocytes, of which the eosinophil is believed to be the most prominent component. Inflammatory sensitization of airway neurons is believed to increase nasal sensitivity, heighten the sense of irritation, and promote fluid secretion, airway narrowing, and bronchoconstriction. Oxidative stress is a hallmark of most acute and chronic inflammatory airway conditions, including viral infections, asthma, rhinitis, and COPD. Asthma and COPD are major chronic diseases related to airway obstruction. The Global Initiative for Chronic Obstructive Lung Disease provides guidelines for the distinction between asthma and COPD. Asthma is believed to be a chronic inflammatory disease wherein the airflow limitation is more or less reversible while it is more or less irreversible in the case of COPD. Asthma is also believed to be triggered by inhalation of sensitizing agents (like allergens) unlike noxious agents (like particles and certain gases) in the case of COPD. Though both are believed to have an inflammatory component, the inflammation in asthma is believed to be mostly eosinophilic and CD-4 driven, while it is believed to be mostly neutrophilic and CD-8 driven in COPD. Emphysema is a type of COPD in which tiny air sacs in the lungs—alveoli—fill up with air. As the air continues to build up in these sacs, they expand, and may break or become damaged and form scar tissue. The patient becomes progressively short of breath.

The retinoic acid-related orphan receptor γ (RORγ) is a member of the ROR subfamily of nuclear receptors which includes three genes; RORA, RORB and RORC (also known as RORγ). The immune system-specific isoform RORγt is restricted to several distinct immune cell types. RORγt is the key lineage-defining transcription factor for the differentiation program of T helper type 17 (Th17) cells, a subset of CD4+T-helper and the most prominent cells in producing a number of inflammatory cytokines, such as IL-17A, IL-17F, IL-22, and IL-23, which are considered as important pathogenic factors for many immune and inflammatory diseases. The RORγt activity modulation results in the modulation of IL-17 dependent immune and inflammatory responses. Compounds able to modulate RORγt activity are expected to provide a therapeutic benefit in the treatment of numerous medical disorders, such as respiratory diseases.

The RORγt, as a promising medical target, has thus been specifically studied and new RORγt modulators have been discovered. For instance, WO2018/138362 discloses new N-{[2-(piperidin-1-yl)phenyl](phenyl)methyl}-2-(3-oxo-3,4-dihydro-2H-1,4-benzoxazin-7-yl) acetamide derivatives as RORγt modulators, and their uses in several therapies including immune, inflammatory, metabolic, fibrotic, and cholestatic diseases.

The control of the release of active drugs into the organism is a further research approach of new therapies currently used in the pharmaceutical field for increasing their bioavailability.

However, there is still a need to identify new ROR modulators having improved pharmacokinetic properties to provide more efficient treatment against ROR-related diseases such as respiratory diseases.

SUMMARY OF THE INVENTION

In this context, the inventors have provided new phosphate derivatives of ROR modulators having improved and advantageous pharmacokinetic properties. The inventors have demonstrated that such phosphate derivatives exhibit an improved solubility and stability in water as well as an improved metabolization in the organism, facilitating thereby the absorption of the ROR modulator in the organism, more particularly in lungs.

The present invention thus provides a compound having the following formula (I):

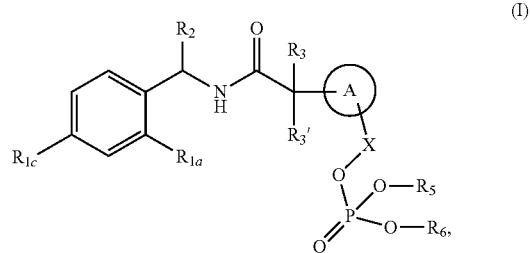

wherein:
A is a ring of the following formula (a):

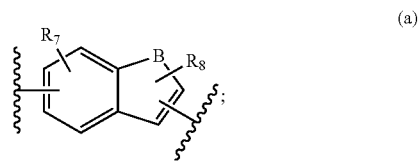

in which:
B represents a NH group, an oxygen atom, or a $SO_2$ group,
$R_7$ represents a hydrogen, a halogen, or a $(C_1\text{-}C_6)$ alkyloxy group, and
$R_8$ represents a hydrogen or a $(C_1\text{-}C_6)$alkyl group,
$R_{1a}$ and $R_{1c}$ represent independently a hydrogen, a $(C_1\text{-}C_6)$alkyl group, a $(C_1\text{-}C_6)$alkyloxy group, a halogen, or a heterocycloalkyl optionally substituted by a $(C_1\text{-}C_6)$ alkyl group;
$R_2$ represents a $(C_1\text{-}C_6)$alkyl group or a ring selected in the group consisting of a cycloalkyl, a heterocycloalkyl, an aryl, and a heteroaryl, said ring being optionally substituted by at least one radical selected in the group
consisting of a $(C_1-C_6)$alkyl group, and a halogen;

$R_3$ and $R_{3'}$ represent independently a hydrogen or a $(C_1-C_6)$alkyl group, or $R_3$ and $R_{3'}$ may form together, with the carbon atom to which they are attached, a cycloalkyl;

X represents a $(C_1-C_6)$alkyl group; and $R_5$ and $R_6$ represent independently a hydrogen or a $(C_1-C_6)$alkyl group; and the stereoisomers, and the pharmaceutical salts thereof.

In a particular embodiment, A has the following formulae $(a_1)$ or $(a_2)$:

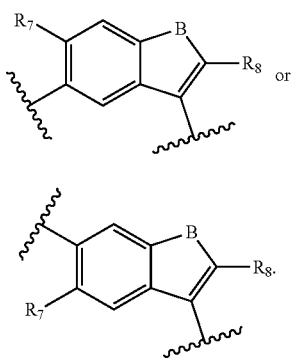

Preferably, B is a NH group.

In a further particular embodiment, a compound of formula (I) is such that:

$R_{1a}$ represents a $(C_1-C_6)$alkyl group, preferably a methyl, a $(C_1-C_6)$alkyloxy group, a halogen, or a heterocycloalkyl, preferably a piperidinyl; and $R_{1c}$ represents a hydrogen, a $(C_1-C_6)$alkyl group, preferably a methyl, a $(C_1-C_6)$alkyloxy group, or a halogen.

In a further particular embodiment, $R_2$ represents a heteroaryl, preferably a furanyl, said heteroaryl being optionally substituted by at least one radical selected in the group consisting of a $(C_1-C_6)$alkyl group and a halogen, preferably a methyl and a chlorine.

In a further particular embodiment, $R_5$ and $R_6$ represent a hydrogen.

In a further particular embodiment, X is a linear $(C_1-C_6)$ alkyl group, preferably a —$CH_2$—$CH_2$— group.

In a further particular embodiment, a pharmaceutically acceptable salt of the compound of formula (I) is a sodium salt, a potassium salt, or a calcium salt, preferably a sodium salt.

In a preferred embodiment of the invention, a compound of formula (I) according to the invention is selected in the group consisting of:

{2-[5-(1-{[(2,4-dimethylphenyl)(5-methylfuran-2-yl) methyl]carbamoyl}cyclopropyl)-1H-indol-3-yl] ethoxy}phosphonic acid;

disodium 2-[5-(1-{[(2,4-dimethylphenyl)(5-methylfuran-2-yl)methyl]carbamoyl}cyclopropyl)-1H-indol-3-yl]ethyl phosphate;

{2-[5-(1-{[(2-methoxy-4-methylphenyl)(phenyl)methyl] carbamoyl}cyclopropyl)-1H-indol-3-yl] ethoxy}phosphonic acid;

disodium 2-[5-(1-{[(2-methoxy-4-methylphenyl)(phenyl) methyl]carbamoyl}cyclopropyl)-1H-indol-3-yl]ethyl phosphate;

{2-[5-(1-{[(2,4-dimethylphenyl)(6-methyl pyridin-2-yl) methyl] carbamoyl} cyclopropyl)-1H-indol-3-yl] ethoxy}phosphonic acid;

disodium {2-[5-(1-{[(2,4-dimethyl phenyl)(6-methyl pyridin-2-yl)methyl] carbamoyl} cyclopropyl)-1H-indol-3-yl] ethoxy} phosphonic acid;

{2-[5-(1-{[(3-chlorophenyl)(2,4-dimethylphenyl)methyl] carbamoyl}cyclopropyl)-1H-indol-3-yl] ethoxy}phosphonic acid;

disodium 2-[5-(1-{[(3-chlorophenyl)(2,4-dimethylphenyl) methyl]carbamoyl}cyclopropyl)-1H-indol-3-yl]ethyl phosphate;

{2-[5-(1-{[(4-methoxy-2-methylphenyl)(phenyl)methyl] carbamoyl}cyclopropyl)-1H-indol-3-yl] ethoxy}phosphonic acid;

disodium 2-[5-(1-{[(4-methoxy-2-methylphenyl)(phenyl) methyl]carbamoyl}cyclopropyl)-1H-indol-3-yl]ethyl phosphate;

(2-{5-[1-({[4-methoxy-2-(pyrrolidin-1-yl)phenyl](phenyl) methyl}carbamoyl)cyclopropyl]-1H-indol-3-yl}ethoxy) phosphonic acid;

disodium 2-{5-[1-({[4-methoxy-2-(pyrrolidin-1-yl)phenyl] (phenyl)methyl}carbamoyl)cyclopropyl]-1H-indol-3-yl}ethyl phosphate {2-[5-(1-{[cyclopropyl (2,4-dimethylphenyl)methyl] carbamoyl}cyclopropyl)-1H-indol-3-yl] ethoxy}phosphonic acid;

disodium 2-[5-(1-{[cyclopropyl(2,4-dimethylphenyl) methyl]carbamoyl}cyclopropyl)-1H-indol-3-yl]ethyl phosphate;

(2-{5-[1-({[4-methyl-2-(morpholin-4-yl) phenyl](phenyl) methyl}carbamoyl) cyclopropyl]-1H-indol-3-yl}ethoxy) phosphonic acid;

disodium 2-{5-[1-({[4-methyl-2-(morpholin-4-yl) phenyl] (phenyl)methyl}carbamoyl) cyclopropyl]-1H-indol-3-yl}ethyl phosphate;

{2-[5-(1-{[(dimethyl-1,2-oxazol-4-yl) (phenyl)methyl]carbamoyl} cyclopropyl)-1H-indol-3-yl] ethoxy} phosphonic acid;

disodium 2-[5-(1-{[(dimethyl-1,2-oxazol-4-yl) (phenyl) methyl]carbamoyl} cyclopropyl)-1H-indol-3-yl] ethyl phosphate;

({5-[({[4-methyl-2-(piperidin-1-yl)phenyl](5-methylfuran-2-yl)methyl}carbamoyl)methyl]-1H-indol-3-yl}methyloxy)phosphonic acid;

disodium ({5-[({[4-methyl-2-(piperidin-1-yl)phenyl](5-methylfuran-2-yl)methyl}carbamoyl)methyl]-1H-indol-3-yl}methyloxy)phosphonic acid;

{2-[5-(1-{[(2,4-di methyl phenyl)(5-chlorofuran-2-yl) methyl] carbamoyl} cyclopropyl)-1H-indol-3-yl] ethoxy}phosphonic acid;

disodium 2-[5-(1-{[(2,4-di methyl phenyl)(5-chlorofuran-2-yl)methyl] carbamoyl} cyclopropyl)-1H-indol-3-yl]ethyl phosphate;

{2-[5-(1-{[(4-methyl-2-(piperidin-1-yl)phenyl)(5-methylfuran-2-yl)methyl]carbamoyl}cyclopropyl)-1H-indol-3-yl]ethoxy}phosphonic acid;

disodium 2-[5-(1-{[(4-methyl-2-(piperidin-1-yl)phenyl)(5-methylfuran-2-yl)methyl] carbamoyl}cyclopropyl)-1H-indol-3-yl]ethyl phosphonate;

2-(5-(1-(((2,4-di methyl phenyl)(5-methylfuran-2-yl) methyl)carbamoyl)cyclopropyl)-1H-indol-3-yl)-2-methylpropyloxy)phosphonic acid; and disodium 2-(5-(1-(((2,4-di methyl phenyl)(5-methylfuran-2-yl)methyl)carbamoyl) cyclopropyl)-1H-indol-3-yl)-2-methylpropyl phosphate.

Another object of the invention is a compound of formula (I) as defined herein for use as a drug. A further object of the invention is a pharmaceutical composition comprising a compound of formula (I) as defined herein, and a pharmaceutically acceptable excipient. In another further particular embodiment, the present invention relates to a compound of formula (I) or a pharmaceutical composition comprising the same for use for treating a respiratory disease, such as neutrophilic asthma, chronic obstructive pulmonary disease (COPD), asthma-COPD overlap syndrome (ACOS), idiopathic pulmonary fibrosis (IPF), and chronic rhinosinusitis with nasal polyps (CRSwNP)

In a particular embodiment, the pharmaceutical composition is in a form of a suspension, a gel, an oil, a powder, an aerosol, or a spray. In a further particular embodiment, the composition is administered by a nasal inhalation.

A further object of the invention is a device comprising a pharmaceutical composition as defined herein. In a preferred embodiment, the device is a dry powder inhaler (DPI) or a metered dose inhaler (MDI).

DETAILED DESCRIPTION OF THE INVENTION

Definitions

Figure 1:
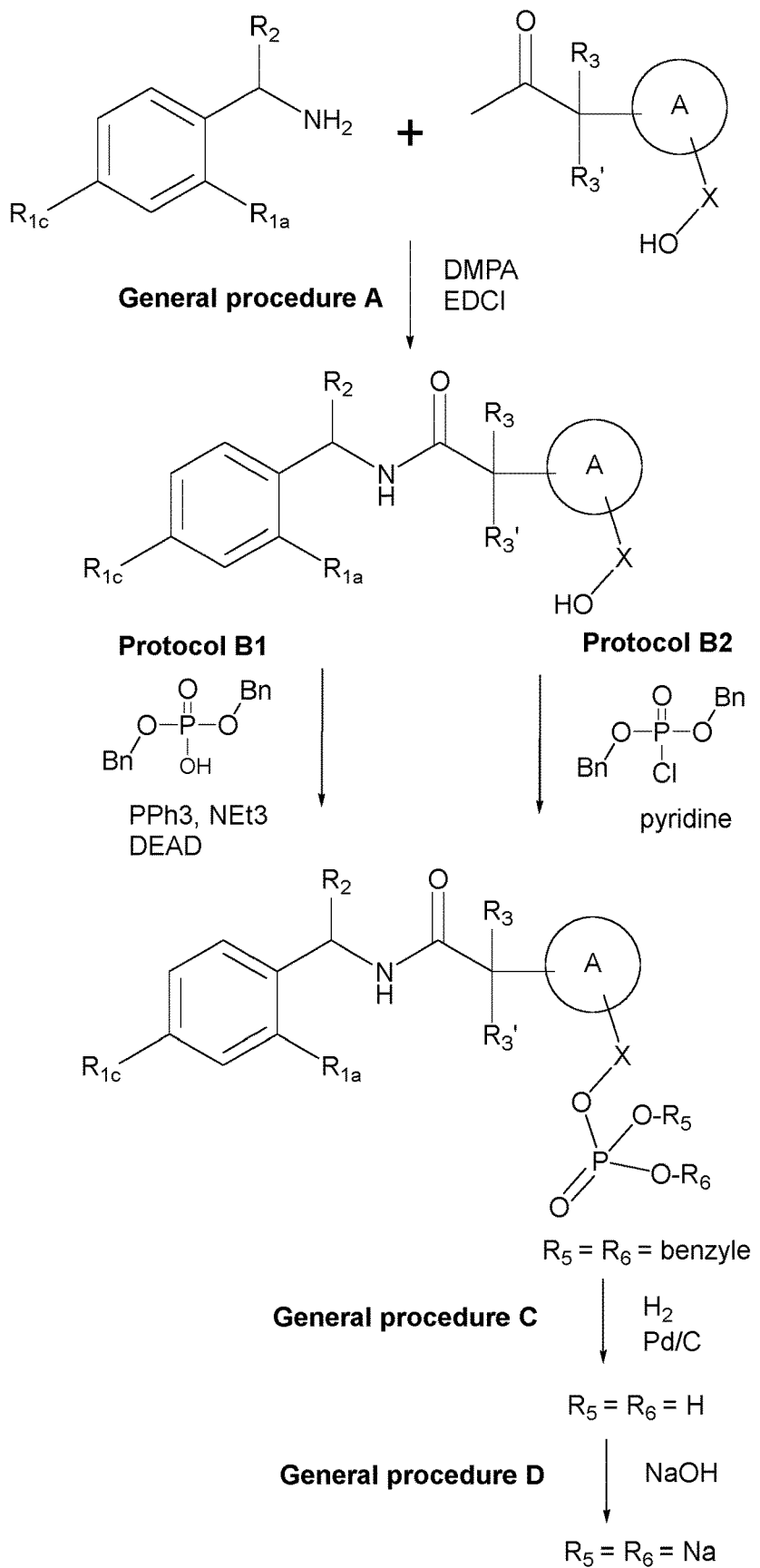
FIG. 1: General synthesis scheme of Compounds of formula (I)

According to the present invention, the terms below have the following meanings:

The terms mentioned herein with prefixes such as for example $C_1$-$C_6$, can also be used with lower numbers of carbon atoms such as $C_1$-$C_2$. If, for example, the term $C_1$-$C_6$ is used, it means that the corresponding hydrocarbon chain may comprise from 1 to 6 carbon atoms, especially 1, 2, 3, 4, 5, or 6 carbon atoms. If, for example, the term $C_1$-$C_3$ is used, it means that the corresponding hydrocarbon chain may comprise from 1 to 3 carbon atoms, especially 1, 2, or 3 carbon atoms.

The term "alkyl" refers to a saturated, linear or branched aliphatic group. The term "($C_1$-$C_6$)alkyl" more specifically means methyl, ethyl, propyl, isopropyl, butyl, pentyl, or hexyl. In a preferred embodiment, the "alkyl" is a methyl.

The term "alkoxy" or "alkyloxy" corresponds to the alkyl group as above defined bonded to the molecule by an —O— (ether) bond. ($C_1$-$C_6$)alkoxy includes methoxy, ethoxy, propyloxy, isopropyloxy, butyloxy, pentyloxy, or hexyloxy. In a preferred embodiment, the "alkoxy" or "alkyloxy" is a methoxy, an ethoxy, a propoxy, an isopropyloxy, more preferably a methoxy.

The term "cycloalkyl" corresponds to a saturated or unsaturated mono-, bi- or tri-cyclic alkyl group comprising between 3 and 20 atoms of carbons. It also includes fused, bridged, or spiroconnected cycloalkyl groups. The term "cycloalkyl" includes for instance cyclopropyl, cyclobutyl, cyclopentyl, and cyclohexyl, preferably cyclopropyl. The term "spirocycloalkyl" includes for instance a spirocyclopropyl.

The term "heterocycloalkyl" corresponds to a saturated or unsaturated cycloalkyl group as above defined further comprising at least one heteroatom such as nitrogen, oxygen, or sulphur atom, preferably at least one nitrogen atom. It also includes fused, bridged, or spiroconnected heterocycloalkyl groups. Representative heterocycloalkyl groups include, but are not limited to dioxolanyl, benzo[1,3]dioxolyl, azetidinyl, oxetanyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, dithiolanyl, azepanyl, thiazolinyl, thiazolidinyl, isothiazolinyl, isothiazolidinyl, dihydropyranyl, tetrahydropyranyl, tetrahydrofuranyl, and tetrahydrothiophenyl. In a preferred embodiment, the heterocycloalkyl group is morpholinyl, piperazinyl, piperidinyl, pyrrolidinyl, tetrahydropyranyl, dithiolanyl and azepanyl groups, more preferably piperidinyl.

The term "aryl" corresponds to a mono- or bi-cyclic aromatic hydrocarbons having from 6 to 12 carbon atoms. For instance, the term "aryl" includes phenyl, naphthyl, or anthracenyl. In a preferred embodiment, the aryl is a phenyl.

The term "cyclic" refers to a cycloalkyl group or an aryl group as above defined.

The term "heteroaryl" as used herein corresponds to an aromatic, mono- or poly-cyclic group comprising between 5 and 14 atoms and comprising at least one heteroatom such as nitrogen, oxygen or sulphur atom. As used herein, the term "heteroaryl" further includes the "fused arylheterocycloalkyl" and "fused heteroarylcycloalkyl". The terms "fused arylheterocycloalkyl" and "fused heteroarylcycloalkyl" correspond to a bicyclic group in which an aryl as above defined or a heteroaryl is respectively bounded to the heterocycloalkyl or the cycloalkyl as above defined by at least two carbons. In other terms, the aryl or the heteroaryl respectively shares a carbon bond with the heterocycloalkyl or the cycloalkyl. Examples of such mono- and poly-cyclic heteroaryl groups may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzoisoxazolyl, oxindolyl, benzoxazolyl, benzoxazolinyl, benzoxazinyl, benzothienyl, benzothiazolyl, benzodiazepinyl, benzazepinyl, benzoxazepinyl, isatinyl, dihydropyridyl, pyrimidinyl, s-triazinyl, oxazolyl, or thiofuranyl. In a preferred embodiment, a heteroaryl is a pyridinyl, pyrimidinyl, furanyl, thiophenyl, quinolinyl, and isoquinolinyl, more preferably a furanyl.

The term "heterocyclic" refers to a heterocycloalkyl group or a heteroaryl group as above defined.

The term "halogen" corresponds to a fluorine, chlorine, bromine, or iodine atom, preferably a fluorine atom or a chlorine atom.

The expression "substituted by at least" means that the radical is substituted by one or several groups of the list.

The expression "optionally substituted" means that the radical is not substituted or substituted by one or several groups of the list.

The "stereoisomers" are isomeric compounds that have the same molecular formula and sequence of bonded atoms, but differ in the 3D-dimensional orientations of their atoms in space. The stereoisomers include enantiomers, diastereoisomers, Cis-trans and E-Z isomers, conformers, tautomers, and anomers. In a preferred embodiment of the invention, the stereoisomers include diastereoisomers and enantiomers.

The "pharmaceutically salts" include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base includes for instance a salt with methylamine, dimethylamine, trimethylamine, piperidine, morpholine or tris-(2-hydroxyethyl)amine. In a preferred embodiment, the salt is a sodium salt, a potassium salt or a calcium salt. In a more preferred embodiment, the salt is a sodium salt. In an even more preferred embodiment, the salt is a disodium salt.

As used herein, the terms "treatment", "treat" or "treating" refer to any act intended to ameliorate the health status of patients such as therapy, prevention, prophylaxis and retardation of a disease, in particular a respiratory disease. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity", "amount", and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

In the present invention, the terms "RORgamma", "RORγ" and "RORg" are used interchangeably. As used herein a "RORγ modulator" refers to a chemical compound that modulates, either directly or indirectly, the activity of RORγ. In particular, the RORγ modulator modulates, in particular inhibits or activates, more particularly inhibits, either directly or indirectly, the activity of RORγ. RORγ modulators include antagonists, inverse agonists and agonists of RORγ, in particular antagonists and inverse agonists.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease, particularly a respiratory disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "pharmaceutically acceptable excipient" refers to any ingredient except active ingredients which are present in a pharmaceutical composition. Its addition may be aimed to confer a particular consistency or other physical or gustative properties to the final product. A pharmaceutically acceptable excipient must be devoid of any interaction, in particular chemical, with the active ingredients.

Compounds

The present invention provides new compounds as ROR modulators.

According to the invention, a compound has the following formula (I):

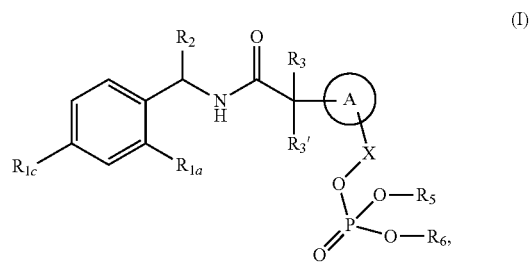

(I)

in which:
A is a ring of the following formula (a):

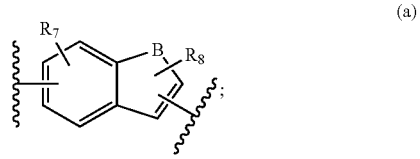

(a)

in which:
B represents a NH group, an oxygen atom, or a $SO_2$ group,
$R_7$ represents a hydrogen, a halogen, or a $(C_1\text{-}C_6)$ alkyloxy group, and
$R_8$ represents a hydrogen or a $(C_1\text{-}C_6)$alkyl group,
$R_{1a}$ and $R_{1c}$ represent independently a hydrogen, a $(C_1\text{-}C_6)$alkyl group, a $(C_1\text{-}C_6)$alkyloxy group, a halogen, or a heterocycloalkyl optionally substituted by a $(C_1\text{-}C_6)$ alkyl group;

$R_2$ represents a $(C_1-C_6)$alkyl group or a ring selected in the group consisting of a cycloalkyl, a heterocycloalkyl, an aryl, and a heteroaryl, said ring being optionally substituted by at least one radical selected in the group consisting of a $(C_1-C_6)$alkyl group, and a halogen;

$R_3$ and $R_{3'}$ represent independently a hydrogen or a $(C_1-C_6)$alkyl group, or $R_3$ and $R_{3'}$ may form together, with the carbon atom to which they are attached, a cycloalkyl;

X represents a $(C_1-C_6)$alkyl group; and $R_5$ and $R_6$ represent independently a hydrogen or a $(C_1-C_6)$alkyl group; and the stereoisomers, and the pharmaceutical salts thereof.

In a particular embodiment, the ring A is linked to the rest of the molecule at positions 3 and 5 of the ring. According to this embodiment, the ring A may be represented by the following formula $(a_1)$:

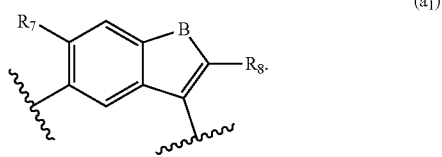

In a further particular embodiment, the ring A is linked to the rest of the molecule in positions 3 and 6 of the ring. According to this embodiment, the ring A may be represented by the following formula $(a_2)$:

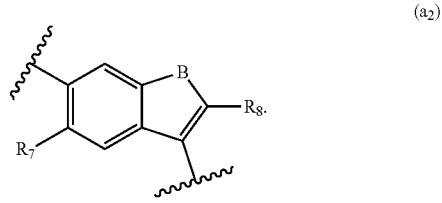

In a preferred embodiment, the ring A is of formula $(a_1)$.

A compound of formula (I) according to the invention is such that B represents a NH group, an oxygen atom, or a $SO_2$ group. If B represents a NH group, then the ring A corresponds to an indolyl. If B represents an oxygen atom, then the ring A corresponds to a benzofuranyl. If B represents a $SO_2$ group, then the ring A corresponds to a benzothiophen-1,1-dioxide.

In a preferred embodiment, B is a NH group.

In a more preferred embodiment, the ring A is of formula $(a_1)$ and B is a NH group. According to this more preferred embodiment, the ring A corresponds to an indolyl group linked to the rest of the molecule at positions 3 and 5 of the ring.

A compound of formula (I) according to the invention is such that $R_7$ represents a hydrogen, a halogen, or a $(C_1-C_6)$alkyloxy group, and $R_8$ represent a hydrogen or a $(C_1-C_6)$alkyl group, preferably a $(C_1-C_4)$alkyl group.

In a preferred embodiment, $R_7$ represents a hydrogen or a fluorine, more preferably a hydrogen.

In a preferred embodiment, $R_8$ represents a hydrogen or a methyl, more preferably a hydrogen. In a more preferred embodiment, the ring A is of formula $(a_1)$, B is a NH group, $R_7$ represents a hydrogen, and $R_8$ represents a hydrogen.

A compound of formula (I) according to the invention is such that $R_{1a}$ and $R_{1c}$ represent independently a hydrogen, a $(C_1-C_6)$alkyl group, a $(C_1-C_6)$alkyloxy group, a halogen, or a heterocycloalkyl, such as an azetidinyl, a pyrrolidinyl, a tetrahydropyranyl, a dithiolanyl, a piperidinyl, an azepanyl, a piperazinyl, and a morpholinyl, said heterocycloalkyl being optionally substituted by a $(C_1-C_6)$alkyl group.

In a particular embodiment, $R_{1a}$ represents a $(C_1-C_6)$alkyl group, a $(C_1-C_6)$alkyloxy group, or a heterocycloalkyl selected in the group consisting of an azetidinyl, a pyrrolidinyl, a piperidinyl, an azepanyl, a piperazinyl, and a morpholinyl, said heterocycloalkyl being optionally substituted by a $(C_1-C_6)$alkyl group. Preferably, $R_{1a}$ represents a $(C_1-C_6)$alkyl group, preferably a methyl, a pyrrolidinyl or a piperidinyl.

In a particular embodiment, $R_{1c}$ represents a $(C_1-C_6)$alkyl group or a $(C_1-C_6)$alkyloxy group. Preferably, $R_{1c}$ represents a $(C_1-C_6)$alkyl group, more preferably a methyl.

In a preferred embodiment, $R_{1a}$ represents a $(C_1-C_6)$alkyl group, preferably a methyl, a $(C_1-C_6)$alkyloxy group, a halogen, or a heterocycloalkyl, preferably a piperidinyl; and $R_1$ represents a hydrogen, a $(C_1-C_6)$alkyl group, preferably a methyl, a $(C_1-C_6)$alkyloxy group, or a halogen. In a particular embodiment, $R_{1a}$ and $R_{1c}$ are identical. Preferably, $R_{1a}$ and $R_{1c}$ represent a $(C_1-C_6)$alkyl group, preferably a methyl.

In a further particular embodiment, $R_{1a}$ and $R_{1c}$ are different. Preferably, $R_{1a}$ is a heterocycloalkyl, preferably a piperidinyl, and $R_{1c}$ is a $(C_1-C_6)$alkyl group, preferably a methyl.

A compound of formula (I) according to the invention is such that $R_2$ represents a $(C_1-C_6)$alkyl group or a ring selected in the group consisting of a cycloalkyl, a heterocycloalkyl, an aryl, and a heteroaryl, said ring being optionally substituted by at least one radical selected in the group consisting of a $(C_1-C_6)$alkyl group, and a halogen.

In a particular embodiment, $R_2$ represents an aryl or a heteroaryl, optionally substituted by at least one radical selected in the group consisting of a $(C_1-C_6)$alkyl group and a halogen.

In a preferred embodiment, $R_2$ represents a phenyl or a heteroaryl chosen among a furanyl, a pyridinyl, a pyrimidinyl, a quinolinyl, an isoquinolinyl, or a thiophenyl, optionally substituted by at least one radical selected in the group consisting of a $(C_1-C_6)$alkyl group and a halogen. In a further preferred embodiment, $R_2$ represents a heteroaryl, preferably a furanyl, said heteroaryl being optionally substituted by at least one radical selected in the group consisting of a $(C_1-C_6)$alkyl group and a halogen, preferably a methyl and a chlorine. In a more preferred embodiment, $R_2$ represents a furanyl substituted by at least one radical selected in the group consisting of a $(C_1-C_6)$alkyl group, preferably a methyl, and a halogen, preferably a chlorine.

A compound of formula (I) according to the invention is such that $R_3$ and $R_{3'}$ represent independently a hydrogen or a $(C_1-C_6)$alkyl group, or $R_3$ and $R_{3'}$ may form together, with the carbon atom to which they are attached, a cycloalkyl.

In a particular embodiment, $R_3$ and $R_{3'}$ represent independently a hydrogen or a $(C_1-C_6)$alkyl group. In a preferred embodiment, $R_3$ and $R_{3'}$ represent a hydrogen.

In a further particular embodiment, $R_3$ and $R_{3'}$ form together, with the carbon atom to which they are attached, a cycloalkyl. Accordingly, the cycloalkyl is spiroconnected to the rest of the molecule. In a preferred embodiment, $R_3$ and $R_{3'}$ form together, with the carbon atom to which they are attached, a cyclopropyl or a cyclobutyl, preferably a cyclopropyl.

A compound of formula (I) according to the invention is such that $R_5$ and $R_6$ represent independently a hydrogen or a $(C_1-C_6)$alkyl group. In a particular embodiment, $R_5$ and $R_6$ represent a hydrogen.

A compound of formula (I) according to the invention is such that X represents a $(C_1-C_6)$alkyl group. As X is substituted on both terminals, it is well understood that the valency 4 of the carbons is respected so that X is a (—$CH_2$—) group when it corresponds to a methyl, X is a (—$CH_2$—$CH_2$—) group when it corresponds to an ethyl, X is a (—$CH_2$—$CH_2$—$CH_2$) when it corresponds to a propyl. In a particular embodiment, X is a saturated linear aliphatic group comprising from 1 to 6 carbon atoms, such as a methyl, an ethyl, a propyl, a butyl, a pentyl, and a hexyl. Preferably, X is a (—$CH_2$)— or a (—$CH_2$—$CH_2$—) group, more preferably a (—$CH_2$—$CH_2$—) group. In a further particular embodiment, X is a saturated branched aliphatic group comprising from 1 to 6 carbon atoms, such as 1-methylethyl (—$CH(CH_3)$—$CH_2$—) and 2-methylpropyl (—$CH_3$—$CH(CH_3)$—$CH_2$—) or 1,1-dimethylethyl (—$C(CH_3)_2$—$CH_2$—). Preferably X is 2-methylpropyl (—$CH_3$—$CH(CH_3)$—$CH_2$—) or 1,1-dimethylethyl (—$C(CH_3)_2$—$CH_2$—).

According to the invention, the compounds of formula (I) further comprise the pharmaceutically acceptable salts as above defined. In a preferred embodiment, the salt is a sodium salt, a potassium salt or a calcium salt. In a more preferred embodiment, the salt is a sodium salt. In an even more preferred embodiment, the salt is a disodium salt.

In a preferred embodiment, a compound of formula (I) is selected in the group consisting of:

Cpd. 1: {2-[5-(1-{[(2,4-dimethylphenyl)(5-methylfuran-2-yl)methyl]carbamoyl}cyclopropyl)-1H-indol-3-yl]ethoxy}phosphonic acid;

Cpd. 2: disodium 2-[5-(1-{[(2,4-dimethylphenyl)(5-methylfuran-2-yl)methyl]carbamoyl}cyclopropyl)-1H-indol-3-yl]ethyl phosphate;

Cpd. 3: {2-[5-(1-{[(2-methoxy-4-methylphenyl)(phenyl)methyl]carbamoyl}cyclopropyl)-1H-indol-3-yl]ethoxy}phosphonic acid;

Cpd. 4: disodium 2-[5-(1-{[(2-methoxy-4-methylphenyl)(phenyl)methyl]carbamoyl}cyclopropyl)-1H-indol-3-yl]ethyl phosphate;

Cpd. 5: {2-[5-(1-{[(2,4-dimethylphenyl)(6-methyl pyridin-2-yl) methyl] carbamoyl} cyclopropyl)-1H-indol-3-yl]ethoxy}phosphonic acid;

Cpd. 6: disodium {2-[5-(1-{[(2,4-dimethyl phenyl)(6-methyl pyridin-2-yl)methyl] carbamoyl} cyclopropyl)-1H-indol-3-yl] ethoxy} phosphonic acid;

Cpd. 7: {2-[5-(1-{[(3-chlorophenyl)(2,4-dimethylphenyl) methyl]carbamoyl}cyclopropyl)-1H-indol-3-yl]ethoxy}phosphonic acid;

Cpd. 8: disodium 2-[5-(1-{[(3-chlorophenyl)(2,4-dimethylphenyl)methyl]carbamoyl}cyclopropyl)-1H-indol-3-yl]ethyl phosphate;

Cpd. 9: {2-[5-(1-{[(4-methoxy-2-methylphenyl)(phenyl)methyl]carbamoyl}cyclopropyl)-1H-indol-3-yl]ethoxy}phosphonic acid;

Cpd. 10: disodium 2-[5-(1-{[(4-methoxy-2-methylphenyl)(phenyl)methyl]carbamoyl}cyclopropyl)-1H-indol-3-yl]ethyl phosphate;

Cpd. 11: (2-{5-[1-({[4-methoxy-2-(pyrrolidin-1-yl)phenyl](phenyl)methyl}carbamoyl)cyclopropyl]-1H-indol-3-yl}ethoxy)phosphonic acid;

Cpd. 12: disodium 2-{5-[1-({[4-methoxy-2-(pyrrolidin-1-yl)phenyl](phenyl)methyl}carbamoyl)cyclopropyl]-1H-indol-3-yl}ethyl phosphate Cpd. 13: {2-[5-(1-{[cyclopropyl (2,4-dimethylphenyl)methyl]carbamoyl}cyclopropyl)-1H-indol-3-yl]ethoxy}phosphonic acid;

Cpd. 14: disodium 2-[5-(1-{[cyclopropyl(2,4-dimethylphenyl)methyl]carbamoyl}cyclopropyl)-1H-indol-3-yl]ethyl phosphate;

Cpd. 15: (2-{5-[1-({[4-methyl-2-(morpholin-4-yl) phenyl](phenyl)methyl} carbamoyl) cyclopropyl]-1H-indol-3-yl}ethoxy) phosphonic acid;

Cpd. 16: disodium 2-{5-[1-({[4-methyl-2-(morpholin-4-yl)phenyl](phenyl)methyl} carbamoyl) cyclopropyl]-1H-indol-3-yl}ethyl phosphate;

Cpd. 17: {2-[5-(1-{[(dimethyl-1,2-oxazol-4-yl) (phenyl)methyl]carbamoyl} cyclopropyl)-1H-indol-3-yl] ethoxy} phosphonic acid;

Cpd. 18: disodium 2-[5-(1-{[(dimethyl-1,2-oxazol-4-yl) (phenyl) methyl]carbamoyl} cyclopropyl)-1H-indol-3-yl]ethyl phosphate;

Cpd. 19: ({5-[({[4-methyl-2-(piperidin-1-yl)phenyl](5-methylfuran-2-yl)methyl}carbamoyl)methyl]-1H-indol-3-yl}methyloxy)phosphonic acid;

Cpd. 20: disodium ({5-[({[4-methyl-2-(piperidin-1-yl)phenyl](5-methylfuran-2-yl)methyl}carbamoyl)methyl]-1H-indol-3-yl}methyloxy)phosphonic acid;

Cpd. 21: {2-[5-(1-{[(2,4-dimethylphenyl)(5-chlorofuran-2-yl)methyl] carbamoyl} cyclopropyl)-1H-indol-3-yl]ethoxy}phosphonic acid;

Cpd. 22: disodium 2-[5-(1-{[(2,4-dimethylphenyl)(5-chlorofuran-2-yl)methyl] carbamoyl} cyclopropyl)-1H-indol-3-yl]ethyl phosphate;

Cpd. 23: {2-[5-(1-{[(4-methyl-2-(piperidin-1-yl)phenyl)(5-methylfuran-2-yl)methyl]carbamoyl}cyclopropyl)-1H-indol-3-yl]ethoxy}phosphonic acid;

Cpd. 24: disodium 2-[5-(1-{[(4-methyl-2-(piperidin-1-yl)phenyl)(5-methylfuran-2-yl)methyl]carbamoyl}cyclopropyl)-1H-indol-3-yl]ethyl phosphonate;

Cpd. 25: 2-(5-(1-(((2,4-dimethylphenyl)(5-methylfuran-2-yl)methyl)carbamoyl)cyclopropyl)-1H-indol-3-yl)-2-methylpropyloxy)phosphonic acid; and Cpd. 26: disodium 2-(5-(1-(((2,4-dimethylphenyl)(5-methylfuran-2-yl)methyl)carbamoyl) cyclopropyl)-1H-indol-3-yl)-2-methylpropyl phosphate.

In a more preferred embodiment, the compound of formula (I) is selected in the group consisting of:

Cpd. 2: disodium 2-[5-(1-{[(2,4-dimethylphenyl)(5-methylfuran-2-yl)methyl]carbamoyl}cyclopropyl)-1H-indol-3-yl]ethyl phosphate, and Cpd. 4: disodium 2-[5-(1-{[(2-methoxy-4-methylphenyl)(phenyl)methyl]carbamoyl}cyclopropyl)-1H-indol-3-yl]ethyl phosphate;

Cpd. 6: disodium {2-[5-(1-{[(2,4-dimethyl phenyl)(6-methyl pyridin-2-yl)methyl] carbamoyl} cyclopropyl)-1H-indol-3-yl] ethoxy} phosphonic acid;

Cpd. 8: disodium 2-[5-(1-{[(3-chlorophenyl)(2,4-dimethylphenyl)methyl]carbamoyl}cyclopropyl)-1H-indol-3-yl]ethyl phosphate;

Cpd. 10: disodium 2-[5-(1-{[(4-methoxy-2-methylphenyl)(phenyl)methyl]carbamoyl}cyclopropyl)-1H-indol-3-yl]ethyl phosphate;

Cpd. 12: disodium 2-{5-[1-({[4-methoxy-2-(pyrrolidin-1-yl)phenyl](phenyl)methyl}carbamoyl)cyclopropyl]-1H-indol-3-yl}ethyl phosphate Cpd. 14: disodium 2-[5-(1-{[cyclopropyl(2,4-dimethylphenyl)methyl]carbamoyl}cyclopropyl)-1H-indol-3-yl]ethyl phosphate;

Cpd. 16: disodium 2-{5-[1-({[4-methyl-2-(morpholin-4-yl)phenyl](phenyl)methyl} carbamoyl) cyclopropyl]-1H-indol-3-yl}ethyl phosphate;

Cpd. 18: disodium 2-[5-(1-{[(dimethyl-1,2-oxazol-4-yl)(phenyl)methyl]carbamoyl} cyclopropyl)-1H-indol-3-yl]ethyl phosphate;

Cpd. 20: disodium ({5-[({[4-methyl-2-(piperidin-1-yl)phenyl](5-methylfuran-2-yl)methyl}carbamoyl)methyl]-1H-indol-3-yl}methyloxy)phosphonic acid;

Cpd. 22: disodium 2-[5-(1-{[(2,4-dimethylphenyl)(5-chlorofuran-2-yl)methyl] carbamoyl} cyclopropyl)-1H-indol-3-yl]ethyl phosphate;

Cpd. 24: disodium 2-[5-(1-{[(4-methyl-2-(piperidin-1-yl)phenyl)(5-methylfuran-2-yl)methyl]carbamoyl}cyclopropyl)-1H-indol-3-yl]ethyl phosphonate; and Cpd. 26: disodium 2-(5-(1-(((2,4-dimethylphenyl)(5-methylfuran-2-yl)methyl)carbamoyl) cyclopropyl)-1H-indol-3-yl)-2-methylpropyl phosphate.

In an even more preferred embodiment, the compound of formula (I) is selected from:

Cpd. 2: disodium 2-[5-(1-{[(2,4-dimethylphenyl)(5-methylfuran-2-yl)methyl]carbamoyl}cyclopropyl)-1H-indol-3-yl]ethyl phosphate, and Cpd. 8: disodium 2-[5-(1-{[(3-chlorophenyl)(2,4-dimethylphenyl)methyl]carbamoyl}cyclopropyl)-1H-indol-3-yl]ethyl phosphate.

In another embodiment, the compound of formula (I) is Cpd. 2: disodium 2-[5-(1-{[(2,4-dimethylphenyl)(5-methylfuran-2-yl)methyl]carbamoyl}cyclopropyl)-1H-indol-3-yl]ethyl phosphate.

The compounds of formula (I) according to the present invention can be prepared according to any chemical routes known from a skilled person, such as general synthetic routes presented in the examples and FIG. 1. It is thus understood that one skilled in the art of organic chemistry can easily synthesize the compounds of formula (I) using appropriate starting materials commercially available or readily synthesized, conventional chemicals reactions, standard and literatures procedures, and experimental conditions.

The compounds of the invention may contain one or more asymmetric centers. The present invention includes stereoisomers (diastereoisomers, enantiomers), pure or mixed, as well as racemic mixtures and geometric isomers, or tautomers of compounds of formula (I). When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are well known and described in the literature.

The compounds of formula (I) can be purified by precipitation or solid/liquid extraction after evaporation of the reaction medium. Further or other purification step can be performed by chromatography over silica gel or by crystallization, when the compound is stable as a solid form, by applying techniques well known in the literature. Moreover, the required purification and/or (re-)crystallization steps that are appropriate for isolating compounds of formula (I) from the reaction mixture, can be used for obtaining amorphous, polymorphous, mono- or poly-crystalline forms. Such polymorphisms may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids. The (re-)crystallisation assays can be performed in panels of different solvents (such as isopropanol, acetone, methanol, diisopropyl ether or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms.

Such a polymorphism study allows characterizing the crystalline form of a compound that is pharmaceutically acceptable for both pharmacological and manufacturing points of view. Certain compounds of formula (I) can be isolated in the form of zwitterions and each of these forms is included in the invention, as well as mixtures thereof. Compounds of formula (I) and their salts can be stable in liquid or solid forms. The present invention includes all solid and liquid forms of formula (I), which includes the amorphous, polymorphic, mono- and poly-crystalline forms. In particular, the compounds of formula (I) can exist in the free form or in the solvated form, i.e. in the form of associations or combinations with one or more molecules of a solvent, for example with pharmaceutically acceptable solvents such as water (hydrates) or ethanol.

Compounds of formula (I) can be obtained as specific salts, solvates, and polymorphs during the final purification step of the compound or, in the case of salts, by incorporating the salt into the previously purified compound. The selection of a compound of formula (I) that is produced according to the methods of the invention as an optimal candidate for drug development can be automated for a comprehensive biopharmaceutical characterization at the scale-up stage and for the solid or liquid formulation that is appropriate for the desired route of administration and therapeutic indication.

Therapeutic Applications

As illustrated by examples, the inventors have demonstrated the therapeutic interest of the phosphate derivatives of the invention. Indeed, the inventors have shown that the compounds according to the present invention have improved solubility and pharmacokinetic properties so that they are useful as RORg modulators.

Therefore, the compounds of formula (I) according to the present invention are useful as a drug.

Accordingly, the present invention relates to a compound as defined herein, for use as a drug or a medicine. The present invention further relates to a pharmaceutical or veterinary composition comprising a compound according to the invention. Preferably, the pharmaceutical composition further comprises a pharmaceutically or veterinary acceptable carrier or excipient. The present invention relates to the use of a compound according to the invention as a drug or a medicine. The invention further relates to a method for treating a disease in a subject, wherein a therapeutically effective amount of a compound according to the invention, is administered to said subject in need thereof. The invention also relates to the use of a compound according to the invention, for the manufacture of a medicine. The invention also relates to a pharmaceutical composition comprising a compound according to the invention for use as a drug. In a preferred embodiment, the compounds of formula (I) according to the invention are used as RORg modulators.

The present invention further provides a pharmaceutical composition comprising a compound of formula (I), and a pharmaceutically acceptable carrier or diluent.

Accordingly, the pharmaceutical compositions may further comprise one or several excipients or vehicles acceptable within a pharmaceutical context (e.g., for liquid formulations, saline solutions, physiological solutions, isotonic solutions).

A further object of the invention is a method for preparing a pharmaceutical composition, comprising admixing a compound of formula (I), with at least one pharmaceutically acceptable carrier, vehicle, or diluent. This method involves, for instance, conventional mixing, dissolving, granulation, dragee-making, levigating, emulsifying, encapsulating, entrapping, lyophilizing processes or spray drying.

The term "carrier", "vehicle", or "excipient" refers to any substance, not itself a therapeutic agent, that is added to a pharmaceutical composition to be used as a carrier, vehicle, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc. Agents or vehicles useful for these formulations (liquid and/or injectable and/or solid) are particularly methylcellulose, hydroxylmethylcellulose, polysorbate 80, mannitol, gelatin, lactose, vegetable oils, liposomes, etc. Acceptable excipients can be chosen among disintegrants, binding agents, adhesives, wetting agents, lubricants, glidants, flavors, dyes, fragrances, stearic acid, magnesium oxide, sodium and calcium salts of phosphoric and sulfuric acids, magnesium carbonate, talc, gelatin, lactose, sucrose, starches, polymers, such as polyvinyl alcohol and polyethylene glycols, and other pharmaceutically acceptable materials added to improve taste, odor or appearance of the composition.

The compositions can be made up in solid or liquid form, such as powders, aerosols, sterile solutions, suspensions or emulsions, and the like. The composition may be presented in a solid preformulation composition wherein the active ingredients are dispersed evenly throughout the composition so that the composition may be readily subdivided into equally effective dosage forms. Additionally, the combined compositions may be delivered using sustained-release formulations.

The compositions can be formulated as suspensions, gels, oils, powders, aerosols, sprays etc., eventually by means of galenic forms or devices assuring a prolonged and/or slow release. For this kind of formulation, agents such as cellulose, carbonates or starches can advantageously be used. In a particular embodiment, the pharmaceutical composition of the invention is in a form of a suspension, a gel, an oil, a powder, an aerosol, or a spray.

The compositions of the present invention can also be formulated in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phophatidylcholines, cardiolipins, phosphatidylethanolamines, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

The pharmaceutical composition of the invention can be administered by an inhalation route including oral and nasal inhalation formulations. In a preferred embodiment, the pharmaceutical composition is administered by a nasal inhalation. Suitable formulations for an oral and nasal inhalation include, without limitation, dry powder inhaler (DPI) formulations, metered dose inhaler (MDI) formulations (including oral and nasal aerosols), nasal sprays, and formulations suitable for nebulization.

For an administration by inhalation, the pharmaceutical composition is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, 1,1,1,2-tetrafluoroethane, 1,1,1,2,3,3,3-heptafluoropropane, carbon dioxide or other suitable gas, alone or in combination. Pressurized aerosols may be formulated as suspensions or solutions, and include an appropriate propellant formulation, and various excipients, such as surfactants, co-solvents, etc. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

A further object of the invention is a device comprising a pharmaceutical composition of the invention as defined herein. The device may be suitable for any administration routes. For instance, for an administration by inhalation, preferably by a nasal inhalation, a suitable device is a dry powder inhaler (DPI) or a metered dose inhaler (MDI). A preferred device of the invention is a dry powder inhaler (DPI) or a metered dose inhaler (MDI).

The present invention further concerns a compound of formula (I) as defined above including any one of the disclosed embodiments or a pharmaceutical composition comprising such compound for preventing and/or treating a respiratory disease. The invention further concerns the use of a pharmaceutical composition as defined herein or a compound of formula (I) as defined above including any one of the disclosed embodiments, for the manufacture of a medicament, a medicine or a drug for the treatment of a respiratory disease. The invention also concerns a method for treating a respiratory disease, in a subject in need thereof, comprising administering an effective amount of a compound of formula (I) as defined herein or a pharmaceutical composition as defined herein.

In a preferred embodiment, such a respiratory disease is selected in the group consisting of neutrophilic asthma, chronic obstructive pulmonary disease (COPD), asthma-COPD overlap syndrome (ACOS), idiopathic pulmonary fibrosis (IPF), and chronic rhinosinusitis with nasal polyps (CRSwNP).

Preferably, the treatment with the compound of formula (I) according to the invention or the pharmaceutical composition according to the invention starts no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 50 weeks, more preferably between 1 day and 30 weeks, still more preferably between 1 day and 15 weeks, even more preferably between 1 day and 10 weeks. In a particular embodiment, the duration of the treatment is of about 1 week. Alternatively, the treatment may last as long as the disease persists. The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.01 mg/day to 1000 mg/day, preferably from 0.1 mg/day to 10 mg/day.

It is understood that the form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

In a further particular embodiment, the compounds of formula (I) can be formulated and/or administered in combination with one or more other therapeutically active substances, marketed or under development, that are selected according to a respiratory disease or any other disorders that may be found associated to said respiratory disease in medical settings and that should be also treated. Such a combined administration includes two possibilities: the two agents are administered to a subject at substantially similar times; or the two agents are administered to a subject at different times, at independent intervals that may or may not overlap or coincide. As such, the invention also relates to a kit-of-parts, comprising a compound of formula (I) as defined herein, in association with another therapeutically active agent, for their simultaneous, separate or sequential use in the therapy, in particular in the treatment of a respiratory disease, preferably selected in the group consisting of neutrophilic asthma, chronic obstructive pulmonary disease (COPD), asthma-COPD overlap syndrome (ACOS), idiopathic pulmonary fibrosis (IPF), and chronic rhinosinusitis with nasal polyps (CRSwNP). The present invention also relates to a pharmaceutical composition comprising a compound of formula (I) as defined herein and at least one therapeutically active agent.

Preferably, the additional therapeutically active agent is an active agent having a biological effect on respiratory diseases.

Further aspects and advantages of the invention will be disclosed in the following experimental section that should be considered as illustrative and not limitative.

EXAMPLES

Chemical names follow IUPAC nomenclature. Starting materials and solvents were purchased from commercial suppliers (Acros Organic, Sigma Aldrich, Combi-Blocks, Fluorochem, Fluka, Alfa Aesar or Lancaster) and were used as received without further purification. Some starting materials can be readily synthesized by a person skilled in the art.

Air and moisture sensitive reactions were carried out under an inert atmosphere of nitrogen, and glassware was oven-dried. No attempts were made to optimize reaction yields.

Thin-layer chromatography (TLC) was done on Merck silica gel 60 UV254 (250 µm) plates. Visualization was accomplished with UV light.

Column chromatography was performed on Geduran silica gel 60 (40-63 µm) from Merck. Melting points (mp) were recorded with a Büchi Melting Point B-545 and are uncorrected. All microwave irradiation experiments were carried out in a Biotage Initiator microwave apparatus. 1H spectra were recorded on Bruker Advance I spectrometer at 300 MHz. Chemical shifts ($\delta$) are reported in ppm (parts per million), by reference to the hydrogenated residues of deuterated solvent as internal standard: 2.50 ppm for DMSO-d6, 7.26 ppm for CDCl3, and 3.31, and 4.78 for Methanol-d4. The spectral splitting patterns are designated as follows: s, singlet; d, doublet; dd, doublet of doublets; ddd, doublet of doublet of doublets; t, triplet; dt, doublet of triplets; q, quartet; m, multiplet; br s, broad singlet. Coupling constants (J) are quoted to the nearest 0.1 Hz.

All tested compounds exhibited 95% chemical purity assessed by HPLC on a Merck HITACHI Lachrom L-7000 series and Merck HITACHI diode array detector L-7455 with a Waters column Symmetry C18 (3.5 µm, 4.6*75 mm) and using a gradient of MeOH/Millipore water containing 0.1% of formic acid. Chromatograms were analyzed with Lachrom software version 890-8800-09.

Mass spectrometry measurements were performed on Alliance 2695 and DAD detector 2998 equipped with an Acquity QDa detector from Waters using a Waters column Symmetry C18 (3.5 µm, 4.6*75 mm) and using a gradient of MeOH/Millipore water containing 0.1% of formic acid (chromatograms were analyzed with Empower 3 software) or they were performed on apparatus equipped with Waters 2545 binary gradient module, Waters 2489 UV/Visible detector and Acquity QDa detector using a Waters column Symmetry C18 (3.5 µm, 4.6*75 mm) and using a gradient of MeOH/Millipore water containing 0.1% of formic acid (chromatograms were analyzed with MassLynx 4.1). Mass Electrospray Ionization were noted ESI+ (positive) or ESI– (negative).

Preparative HPLC were performed on apparatus equipped with Waters 2545 binary gradient module, Waters 2489 UV/Visible detector, Acquity QDa detector and Waters 2767 sample manager using a Waters column SymmetryPrep C18 (7 µm, 19*150 mm) and using a gradient of MeOH/Millipore water containing 0.1% of formic acid (chromatograms were analyzed with MassLynx 4.1). All solvents are HPLC grade.

The compounds of the invention are prepared according to the general methods and general protocols of synthesis given below. Representative procedures suitable for the preparation of compounds of formula (I) are outlined in the reaction scheme (FIG. 1).

Starting material can be synthetized according to methods previously disclosed as specified in the protocols or are commercially available. 1-[3-(2-Hydroxyethyl)-1H-indol-5-yl]cyclopropane-1-carboxylic acid was obtained following the procedure described in WO2018138362.

As represented by FIG. 1, the synthetic route to the compounds of the invention comprises the following steps:

(1) an O-alkylation of the hydroxyl group of starting material with dibenzyl chlorophosphonate (Protocol B1) or bis(benzyloxy)phosphinic acid (Protocol B2);

(2) debenzylation by catalytic hydrogenation to provide compound according to the invention in which $R_5=R_6=H$;

(3) preparation of the salt to provide compound according to the invention

Reagents and conditions may be adapted and additional steps employed to produce further compounds encompassed in the present invention having alternative substituent groups, or for achieving such compounds at higher yield and/or of higher purity.

Example 1: Synthesis of Intermediates for the Synthesis of Compounds According to the Invention The general treatments and purification steps are carried out according to techniques well known by a person skilled in the art or such as those described in the literature: the reaction was quenched either with water, brine or sat. NH4Cl. The aqueous layer was extracted three times with a non-water miscible solvent (e.g. diethylether (Et2O), ethyl acetate (EtOAc), dichloromethane ($CH_2Cl2$)). The organic layer was dried over MgSO4, filtered and the solution was concentrated under reduced pressure. Purification of the crude material was realized by purification on silica gel column chromatography using standard mixture systems notified in the different protocols.

General Procedure A: Synthesis of Amides

The amides used as starting materials in FIG. 1 were prepared according to techniques well known by a person skilled in the art.

To a solution of the amine (1 eq) and 1-[3-(2-hydroxyethyl)-1H-indol-5-yl]cyclopropane-1-carboxylic acid (1 eq) in dimethylformamide (DMF) were added dimethylaminopyridine (DMAP) (1.1 eq) and 1-ethyl-3-(3-dimethylaminopropyl)carbodiimide hydrochloride (EDCl, HCl)(1.1 eq). The reaction was stirred at room temperature (rt) for 3 h-5 h. The mixture was quenched with water and extracted with adequate solvent. Combined organic layer was washed with NH4Cl sol., brine, dried over MgSO4 and concentrated under reduced pressure. The product was purified by column chromatography.

General Procedure B: Synthesis of Dibenzylphosphonates

Protocol B1: O-alkylation with bis(benzyloxy)phosphinic acid

To a solution of the carboxamide (1 eq), triphenylphosphine (2 eq), triethylamine (4 eq) and bis(benzyloxy)phosphinic acid (2 eq) in tetrahydrofuran (THF) was added diethylazodicarboxylate (DEAD) (2 eq). The reaction was stirred overnight at room temperature. The mixture was concentrated under reduced pressure. The crude product was purified by column chromatography to afford dibenzyl phosphate.

Protocol B2: O-Alkylation with Dibenzyl Chlorophosphonate

To a solution of carboxamide (0.24 g, 0.507 mmol) and pyridine (5 eq) in acetonitrile (ACN) was added dropwise a solution of dibenzyl chlorophosphonate (6.2 eq) in acetonitrile (1 mL for 1 mmol of carboxamide). The reaction was stirred at 50° C. for 2 h.

The mixture was quenched with water and extracted twice with EtOAc. Combined organic layer was washed twice with NH4Cl sol., brine, dried over MgSO4 and concentrated under reduced pressure. The crude was purified by column chromatography.

General Procedure C: Synthesis of Phosphonic Acids

To a solution of dibenzylphosphonate in ethanol was added a catalytic amount of Pd/C. The reaction mixture was stirred at room temperature for one hour under hydrogen at atmospheric pressure.

After completion of the reaction, the catalyst was removed by filtration. The filtrate was concentrated to dryness to afford the corresponding phosphonic acid. The crude product crystallized.

General Procedure D: Synthesis of Phosphonates

To a solution of phosphonic acid in methanol were added a 2N solution of sodium hydroxide (1 mL for 1 mmol of phosphonic acid). The reaction mixture was stirred at room temperature for two hours. The mixture was concentrated under reduced pressure and lyophilized to afford phosphonate as disodium salt.

In the following, compounds termed "Ex. X" are intermediate compounds used for the synthesis of compounds of the present invention.

Intermediate Ex.1: Preparation of dibenzyl 2-[5-(1-{[(2,4-dimethylphenyl)(5-methylfuran-2-yl)methyl]carbamoyl}cyclopropyl)-1h-indol-3-yl]ethyl phosphate To a solution of N-[(2,4-dimethylphenyl)(5-methylfuran-2-yl)methyl]-1-[3-(2-hydroxyethyl)-1H-indol-5-yl]cyclopropane-1-carboxamide (Cpd.A—0.1 g, 0.226 mmol) (protocol of synthesis disclosed by WO2018/138362) in acetonitrile (2 mL) were successively added ethylbis(propan-2-yl)amine (0.197 mL, 1.13 mmol) and dibenzyl chlorophosphonate (0.402 g, 1.356 mmol). After 18 hours of stirring at room temperature, more ethylbis(propan-2-yl)amine (0.197 mL, 1.13 mmol) and dibenzyl chlorophosphonate (0.402 g, 1.356 mmol) were added and the reaction mixture was further stirred for 18 h00 at 50° C.

The reaction mixture was cooled to room temperature (rt), concentrated to dryness and the residue was purified by column chromatography eluting with cylcohexane7/acetone3 (70/30) to afford dibenzyl 2-[5-(1-{[(2,4-dimethylphenyl)(5-methylfuran-2-yl)methyl]carbamoyl}cyclopropyl)-1H-indol-3-yl]ethyl phosphate (Ex.1) as a colorless oil (0.061 g, 0.087 mmol). Yield: 38%

1H NMR (DMSO-d6): 0.99-1.04 (m, 2H), 1.29-1.37 (m, 2H), 2.08 (s, 3H), 2.12 (s, 3H), 2.17 (s, 3H), 2.99 (t, 2H, J=6.9 Hz), 4.16 (q, 2H, J=7.5 Hz), 4.92 (s, 2H), 4.95 (s, 2H), 5.72 (d, 1H, J=2.7 Hz), 5.86 (dd, 1H, J=3 Hz, J=0.9 Hz), 6.08 (d, 1H, J=8.1 Hz), 6.69 (d, 1H, J=8.4 Hz), 6.76 (d, 1H, J=7.8 Hz), 6.85-6.88 (m, 1H), 6.90-6.92 (m, 1H), 7.10 (dd, 1H, J=8.1 Hz, J=1.5 Hz), 7.18 (d, 1H, J=2.4 Hz), 7.24-7.37 (m, 11H), 7.52-7.54 (m, 1H), 10.95 (br(s), 1H)

m/z (ESI+): 725 (M+Na)+ (calc. mass: 702)

Intermediate Ex.2: Preparation of dibenzyl 2-[5-(1-{[(2-methoxy-4-methylphenyl) (phenyl)methyl]carbamoyl} cyclopropyl)-1h-indol-3-yl]ethyl phosphate

| Cpd. | Starting compounds, Reaction conditions and purification Yield, MP, Appearance, $^1$H NMR (solvent) data, Mass (ESI+ or ESI−) data |
|---|---|
| Ex.2a | 1-[3-(2-hydroxyethyl)-1H-indol-5-yl]-N-[(2-methoxy-4-methylphenyl) (phenyl)methyl]cyclopropane-1-carboxamide<br>From (2-methoxy-4-methylphenyl)(phenyl)methanamine (protocol of synthesis disclosed in WO2016/102633) (0.363 g, 1.376 mmol) and 1-[3-(2-hydroxyethyl)-1H-indol-5-yl]cyclopropane-1-carboxylic acid (0.338 g, 1.376 mmol) according to General procedure A. The reaction was stirred at rt for 3 h. The crude product was purified by column chromatography eluting with dichloromethane/MeOH (100 to 95/5) and lyophilized to provide 1-[3-(2-hydroxyethyl)-1H-indol-5-yl]-N-[(2-methoxy-4-methylphenyl) (phenyl)methyl]cyclopropane-1-carboxamide Ex.2a (0.34 g, 0.748 mmol) as a white solid.<br>Yield: 54%<br>mp: 89-98° C.<br>1H NMR (DMSO-d6): 1.06-1.09 (m, 2H), 1.33-1.46 (m, 2H), 2.22 (s, 3H), 2.86 (t, 2H, J = 7.5 Hz), 2.90 (s, 3H), 3.59-3.70 (m, 2H), 4.63 (t, 1H, J = 5.4 Hz), 6.03 (d, 1H, J = 9.3 Hz), 6.60 (s, 1H), 6.68 (d, 1H, J = 7.5 Hz), 7.03 (d, 2H, J = 7.5 Hz), 7.10-7.24 (m, 7H), 7.39 (d, 1H, J = 8.1 Hz), 7.60 (s, 1H), 10.90 (d, 1H, J = 1.8 Hz).<br>m/z (ESI+): 455.3 (M + H)+, 477.2 (M + Na)+, 931.6 (2M + Na)+ (calc. mass: 454). |
| Ex.2 | dibenzyl 2-[5-(1-{[(2,4-dimethylphenyl)(5-methylfuran-2-yl)methyl] carbamoyl} cyclopropyl)-1H-indol-3-yl]ethyl phosphate<br>From 1-[3-(2-hydroxyethyl)-1H-indol-5-yl]-N-[(2-methoxy-4-methylphenyl)(phenyl)methyl]cyclopropane-1-carboxamide Ex.2a (0.1 g, 0.22 mmol according to Protocol B1. The crude product was purified by column chromatography eluting with dichloromethane/EtOAc (8/2) to provide dibenzyl 2-[5-(1-{[(2-methoxy-4-methylphenyl)(phenyl)methyl]carbamoyl}cyclopropyl)-1H-indol-3-yl]ethyl phosphate Ex.2 (0.1 g, 0.14 mmol) as a colourless oil.<br>Yield: 63%<br>1H NMR (DMSO-d6): 1.04-1.07 (m, 2H), 1.32-1.42 (m, 2H), 2.20 (s, 3H), 2.89 (s, 3H), 3.02 (t, 2H, J = 6.6 Hz), 4.13-4.21 (m, 2H), 4.94 (d, 2H, J = 2.1 Hz), 4.98 (d, 2H, J = 2.1 Hz), 6.03 (d, 1H, J = 9.3 Hz), 6.58 (s, 1H), 6.67 (d, 1H, J = 7.5 Hz), 7.02 (d, 2H, J = 7.5 Hz), 7.09-7.35 (m, 16H), 7.42 (d, 1H, J = 8.7 Hz), 7.59 (s, 1H), 11.01 (d, 1H, J = 2.1 Hz).<br>m/z (ESI+): 715.4 (M + H) |

Intermediate Ex.3: Preparation of dibenzyl 2-[5-(1-{[(2,4-dimethylphenyl)(6-methylpyridin-2-yl) methyl]carbamoyl}cyclopropyl)-1H-indol-3-yl]ethyl phosphate

| Cpd. | Starting compounds, Reaction conditions and purification Yield, MP, Appearance, $^1$H NMR (solvent) data, Mass (ESI+ or ESI−) data |
|---|---|
| Ex.3a | N-[(2,4-dimethylphenyl)(6-methylpyridin-2-yl)methyl]-1-[3-(2-hydroxyethyl)-1H-indol-5-yl]cyclo-propane-1-carboxamide<br>From (2,4-dimethylphenyl)(6-methylpyridin-2-yl)methanamine (protocol of synthesis disclosed in WO2018/138362) (0.306 g, 1.023 mmol) and 1-[3-(2-hydroxyethyl)-1H-indol-5-yl]cyclopropane-1-carboxylic acid (0.251 g, 1.023 mmol) according to General procedure A. The reaction was stirred at rt for 4 h. The crude product was purified by column chromatography eluting with dichloromethane/MeOH (100 to 95/5) and lyophilized to provide N-[(2,4-dimethylphenyl)(6-methylpyridin-2-yl)methyl]-1-[3-(2-hydroxyethyl)-1H-indol-5-yl]cyclo-propane-1-carboxamide Ex.3a (0.35 g, 0.772 mmol) as a white powder.<br>Yield: 75%<br>mp:93-100° C.<br>1H NMR (DMSO-d6): 1.01-1.06 (m, 2H), 1.30-1.35 (m, 2H), 2.00 (s, 3H), 2.17 (s, 3H), 2.31 (s, 3H), 2.86 (t, 2H, J = 7.8 Hz), 3.59-3.66 (m, 2H), 4.61 (t, 1H, J = 5.4 Hz), 5.95 (d, 1H, J = 6.6 Hz), 6.73 (d, 1H, J = 7.8 Hz), 6.83-6.89 (m, 2H), 6.90 (br(s), 1H), 6.99 (d, 1H, J = 7.5 Hz), 7.13 (dd, 1H, J = 8.1 Hz, J = 1.5 Hz), 7.20 (d, 1H, J = 2.1 Hz), 7.40 (d, 1H, J = 8.4 Hz), 7.51 (t, 1H, J = 7.8 Hz), 7.58 (d, 1H, J = 1.5 Hz), 7.70 (d, 1H, J = 6.6 Hz), 10.88 (s, 1H).<br>m/z (ESI+): 454.3 (M + H)+, 476.2 (M + Na)+, 929.6 (2M + Na)+ (calc. mass: 453). |

-continued

| Cpd. | Starting compounds, Reaction conditions and purification<br>Yield, MP, Appearance, ¹H NMR (solvent) data, Mass (ESI+ or ESI−) data |
|---|---|
| Ex.3 | dibenzyl 2-[5-(1-{[(2,4-dimethylphenyl)(6-methylpyridin-2-yl)methyl]carbamoyl}cyclopropyl)-1H-indol-3-yl]ethyl phosphate<br>From N-[(2,4-dimethylphenyl)(6-methylpyridin-2-yl)methyl]-1-[3-(2-hydroxyethyl)-1H-indol-5-yl]cyclopropane-1-carboxamide Ex.3a (0.316 g, 0.697 mmol according to Protocole B1. The crude was purified by column chromatography eluting with dichloromethane/EtOAc (8/2) to provide dibenzyl 2-[5-(1-{[(2,4-dimethylphenyl)(6-methylpyridin-2-yl)methyl]carbamoyl}cyclopropyl)-1H-indol-3-yl]ethyl phosphate Ex.3 (0.235 g, 0.329 mmol) as a colourless oil.<br>Yield: 47%.<br>1H NMR (DMSO-d6): 0.97-1.07 (m, 2H), 1.29-1.32 (m, 2H), 1.97 (s, 3H), 2.17 (s, 3H), 2.30 (s, 3H), 3.03 (t, 2H), 4.15-4.19 (m, 2H), 4.93 (s, 2H), 4.95 (s, 2H), 5.93 (d, 1H, J = 6.3 Hz), 6.72 (d, 1H, J = 7.8 Hz), 6.81-6.87 (m, 3H), 6.95 (d, 1H, J = 7.5 Hz), 7.16 (dd, 1H, J = 8.1 Hz, J = 1.5 Hz), 7.24 (d, 1H, J = 2.4 Hz), 7.27-7.35 (m, 10H), 7.43 (d, 1H, J = 8.1 Hz), 7.49 (t, 1H, J = 7.8 Hz), 7.59 (s, 1H), 7.72 (d, 1H, J = 6.6 Hz), 11.01 (d, 1H, J = 2.1 Hz).<br>m/z (ESI+): 714.4 (M + H)+, 736.4 (M + Na)+ (calc, mass: 713). |

Intermediate Ex.4: Preparation of dibenzyl 2-[5-(1-{[(3-chlorophenyl)(2,4-dimethylphenyl)methyl]carbamoyl}cyclopropyl)-1H-indol-3-yl]ethyl phosphate

| Cpd. | Starting compounds, Reaction conditions and purification<br>Yield, MP, Appearance, ¹H NMR (solvent) data, Mass (ESI+ or ESI−) data |
|---|---|
| Ex.4a | N-[(3-chlorophenyl)(2,4-dimethylphenyl)methyl]-1-[3-(2-hydroxyethyl)-1H-indol-5-yl]cyclopropane-1-carboxamide<br>From (3-chlorophenyl)(2,4-dimethylphenyl)methanamine (protocol of synthesis disclosed in WO2018/138362) (0.1 g, 0.407 mmol) and 1-[3-(2-hydroxyethyl)-1H-indol-5-yl]cyclopropane-1-carboxylic acid (0.1 g, 0.407 mmol) according to General procedure A. The reaction was stirred at rt for 5 h. The crude product was purified by column chromatography eluting with dichloromethane/EtOAc (8/2) and lyophilized to provide N-[(3-chlorophenyl)(2,4-dimethylphenyl)methyl]-1-[3-(2-hydroxyethyl)-1H-indol-5-yl]cyclopropane-1-carboxamide Ex.4a (0.128 g, 0.271 mmol) as a white solid.<br>Yield: 66%<br>mp: 74.8-87.1° C.<br>1H NMR (DMSO-d6): 1.04-1.08 (m, 2H), 1.35-1.39 (m, 2H), 2.12 (s, 3H), 2.21 (s, 3H), 2.83 (t, 2H, J = 7.32 Hz), 3.59-3.66 (m, 2H), 4.61 (t, 1H, J = 5.4 Hz), 6.20 (d, 1H, J = 8.28 Hz), 6.69 (d, 1H, J = 7.83 Hz), 6.87-7.15 (m, 7H), 7.26-7.36 (m, 3H), 7.55 (s, 1H), 10.82 (d, 1H, J = 1.62 Hz).<br>m/z (ESI+): 473.2 (M + H)+, 495.2 (M + Na)+ (calc, mass: 473). |
| Ex.4 | dibenzyl 2-[5-(1-{[(3-chlorophenyl)(2,4-dimethylphenyl)methyl]carbamoyl}cyclopropyl)-1H-indol-3-yl]ethyl phosphate<br>From N-[(3-chlorophenyl)(2,4-dimethylphenyl)methyl]-1-[3-(2-hydroxyethyl)-1H-indol-5-yl]cyclopropane-1-carboxamide Ex.4a (0.24 g, 0.507 mmol) according to Protocole B2. The crude product was purified by column chromatography eluting with dichloromethane/MeOH (gradient: 100/0 to 99/1) to provide dibenzyl 2-[5-(1-{[(3-chlorophenyl)(2,4-dimethylphenyl)methyl]carbamoyl}cyclopropyl)-1H-indol-3-yl]ethyl phosphate Ex.4 (0.1 g, 0.136 mmol) as a colourless oil.<br>Yield: 27%.<br>1H NMR (DMSO-d6): 1.02-1.07 (m, 2H), 1.34-1.37 (m, 2H), 2.11 (s, 3H), 2.18 (s, 3H), 3.01 (t, 2H, J = 6.96 Hz), 4.17 (q, 2H, J = 7.14 Hz), 4.93-4.97 (m, 4H), 6.20 (d, 1H, J = 8.31 Hz), 6.70 (d, 1H, J = 7.86 Hz), 6.85 (d, 1H, J = 7.59 Hz), 6.94-6.97 (m, 2H), 7.01-7.06 (m, 2H), 7.12 (dd, 1H, J = 8.37 Hz, J = 1.62 Hz), 7.19 (d, 1H, J = 2.25 Hz), 7.23-7.38 (m, 13H), 7.56 (br(s), 1H), 10.94 (dd, 1H, J = 2.01 Hz).<br>m/z (ESI+): 733.3 (M + H)+, 755.3 (M + Na)+ (calc, mass: 733). |

Intermediate Ex.5: Preparation of dibenzyl 2-[5-(1-{[(4-methoxy-2-methylphenyl)(phenyl)methyl]carbamoyl}cyclopropyl)-1H-indol-3-yl]ethyl phosphate

| Cpd. | Starting compounds, Reaction conditions and purification Yield, MP, Appearance, ¹H NMR (solvent) data, Mass (ESI+ or ESI−) data |
|---|---|
| Ex.5a | 1-[3-(2-hydroxyethyl)-1H-indol-5-yl]-N-[(4-methoxy-2-methylphenyl)(phenyl)methyl]cyclopropane-1-carboxamide<br>From (4-methoxy-2-methylphenyl)(phenyl)methanamine (protocol of synthesis disclosed in WO2016/102633) (0.4 g, 1.06 mmol), and 1-[3-(2-hydroxyethyl)-1H-indol-5-yl]cyclopropane-1-carboxylic acid (0.26 g, 1.062 mmol) according to General procedure A. The reaction was stirred at rt for 5 h. The crude was purified by column chromatography eluting with dichloromethane/EtOAc (100/0 to 70/30) and lyophilized to afford 1-[3-(2-hydroxyethyl)-1H-indol-5-yl]-N-[(4-methoxy-2-methylphenyl)(phenyl)methyl]cyclopropane-1-carboxamide Ex.5a (0.365 g, 0.803 mmol) as a white foam.<br>Yield: 75%<br>mp: 70.2-88.8° C.<br>1H NMR (DMSO-d6): 1.04-1.08 (m, 2H), −643158.00 (m, 2H), 2.12 (s, 3H), 2.84 (t, 2H, J = 7.41 Hz), 3.60-3.66 (m, 2H), 3.69 (s, 3H), 4.63 (t, 2H, J = 5.43 Hz), 6.15 (d, 1H, J = 8.37 Hz), 6.61-6.65 (m, 2H), 6.70-6.73 (m, 2H), 7.02-7.04 (m, 2H), 7.11 (dd, 1H, J = 8.31 Hz, J = 1.59 Hz), 7.15 (d, 1H, J = 2.19 Hz), 7.18-7.33 (m, 4H), 7.57 (br(s), 1H), 10.83 (d, 1H, J = 1.77 Hz).<br>m/z (ESI+): 455.2 (M + H)+, 477.2 (M + Na)+ (calc, mass: 454). |
| Ex.5 | dibenzyl 2-[5-(1-{[(4-methoxy-2-methylphenyl)(phenyl)methyl]carbamoyl}cyclopropyl)-1H-indol-3-yl]ethyl phosphate<br>From 1-[3-(2-hydroxyethyl)-1H-indol-5-yl]-N-[(4-methoxy-2-methylphenyl)(phenyl)methyl]cyclopropane-1-carboxamide Ex.5a (0.325 g, 0.715 mmol), according to Protocol B1. The crude product was purified by column chromatography eluting with dichloromethane/EtOAc (7/3) to provide a colourless oil which was purified by preparative LC with H20 (+0.1% formic acid)/MeOH (+0.1% formic acid) (gradient 50/50 to 0/100) to afford dibenzyl 2-[5-(1-{(4-methoxy-2-methylphenyl)(phenyl)methyl]carbamoyl}cyclopropyl)-1H-indol-3-yl]ethyl phosphate Ex.5 (0.246 g, 0.344 mmol) as a colourless gum.<br>Yield: 48%.<br>1H NMR (DMSO-d6): 1.02-1.06 (m, 2H), 1.35-1.38 (m, 2H), 2.11 (s, 3H), 3.01 (t, 2H, J = 6.84 Hz), 3.66 (s, 3H), 4.17 (q, 2H, J = 7.05 Hz), 4.96 (d, 4H, J = 8.1 Hz), 6.15 (d, 1H, J = 8.25 Hz), 6.59-6.73 (m, 4H), 7.02 (d, 2H, J = 7.2 Hz), 7.12-7.38 (m, 16H), 7.58 (s, 1H), 10.95 (d, 1H, J = 1.95 Hz).<br>m/z (ESI+): 737.3 (M + Na)+ (calc, mass: 714). |

Intermediate Ex.6: Preparation of dibenzyl 2-{5-[1-({[4-methoxy-2-(pyrrolidin-1-yl)phenyl](phenyl)methyl}carbamoyl)cyclopropyl]-1H-indol-3-yl}ethyl phosphate

| Cpd. | Starting compounds, Reaction conditions and purification Yield, MP, Appearance, ¹H NMR (solvent) data, Mass (ESI+ or ESI−) data |
|---|---|
| Ex.6a | carboxamide<br>From [4-methoxy-2-(pyrrolidin-1-yl)phenyl](phenyl)methanamine (protocol of synthesis disclosed in WO2016/102633) (0.3 g, 0.941 mmol), and 1-[3-(2-hydroxyethyl)-1H-indol-5-yl]cyclopropane-1-carboxylic acid (0.231 g, 0.941 mmol) according to General procedure A. The reaction was stirred at rt for 5 h. The crude product was purified by column chromatography eluting with dichloromethane/EtOAc (100/0 to 70/30) and lyophilized to provide 1-[3-(2-hydroxyethyl)-1H-indol-5-yl]-N-{[4-methoxy-2-(pyrrolidin-1-yl)phenyl](phenyl)methyl}cyclopropane-1-carboxamide Ex.6a (0.156 g, 0.306 mmol) as an off-white solid.<br>Yield: 32%<br>mp: 232.5-239.7° C.<br>1H NMR (DMSO-d6): 1.03-1.13 (m, 4H), 1.22-1.39 (m, 3H), 1.44-1.47 (m, 1H), 2.10-2.17 (m, 2H), 2.33-2.40 (m, 2H), 2.85 (t, 2H, J = 7.47 Hz), 3.58-3.66 (m, 2H), 3.68 (s, 3H), 4.64 (t, 1H, J = 5.43 Hz), 6.22 (d, 1H, J = 8.82 Hz), 6.56-6.60 (m, 2H), 7.02-7.07 (m, 3H), 7.13-7.18 (m, 4H), 7.24-7.29 (m, 2H), 7.35 (d, 1H, J = 8.31 Hz), 7.62 (br(s), 1H), 10.86 (d, 1H, J = 1.95 Hz)<br>m/z (ESI+): 510.3 (M + H)+, 532.3 (M + Na)+ (calc, mass: 509). |

-continued

| Cpd. | Starting compounds, Reaction conditions and purification<br>Yield, MP, Appearance, $^1$H NMR (solvent) data, Mass (ESI+ or ESI−) data |
|---|---|
| Ex.6 | dibenzyl 2-{5-[1-({[4-methoxy-2-(pyrrolidin-1-yl)phenyl](phenyl)methyl}carbamoyl)cyclopropyl]-1H-indol-3-yl}ethyl phosphate<br>From 1-[3-(2-hydroxyethyl)-1H-indol-5-yl]-N-{[4-methoxy-2-(pyrrolidin-1-yl)phenyl](phenyl)methyl}cyclopropane-1-carboxamide Ex.6a (0.141 g, 0.277 mmol) according to Protocole B1. The crude product was purified on successive silica gel column with dichloromethane/EtOAc (7/3) and with dichloromethane/MeOH (gradient 100/0 to 90/10) to provide dibenzyl 2-{5-[1-({[4-methoxy-2-(pyrrolidin-1-yl)phenyl](phenyl)methyl}carbamoyl)-cyclopropyl]-1H-indol-3-yl}ethyl phosphate Ex.6 (0.083 g, 0.108 mmol).<br>Yield: 39%, appearance: colourless gum.<br>1H NMR (DMSO-d6): 0.98-1.09 (m, 4H), 1.18-1.49 (m, 4H), 2.07-2.14 (m, 2H), 2.27-2.35 (m, 2H), 3.01 (t, 2H, J = 6.96 Hz), 3.66 (s, 3H), 4.12-4.20 (m, 2H), 4.97 (d, 4H, J = 8.13 Hz), 6.23 (d, 1H, J = 8.73 Hz), 6.54-6.59 (m, 2H), 7.01-7.39 (m, 20H), 7.61 (s, 1H), 10.98 (d, 1H, J = 2.04 Hz).<br>m/z (ESI+): 770.4 (M + H)+, 792.4 (M + Na)+ (calc. mass: 769). |

Intermediate Ex.7: Preparation of dibenzyl 2-[5-(1-{[cyclopropyl(2,4-dimethylphenyl)methyl]carbamoyl}cyclopropyl)-1H-indol-3-yl]ethyl phosphate

| Cpd. | Starting compounds, Reaction conditions and purification<br>Yield, MP, Appearance, $^1$H NMR (solvent) data, Mass (ESI+ or ESI−) data |
|---|---|
| Ex.7a | N-[cyclopropyl(2,4-dimethylphenyl)methyl]-1-[3-(2-hydroxyethyl)-1H-indol-5-yl]cyclopropane-1-carboxamide<br>From cyclopropyl(2,4-dimethylphenyl)methanamine (0.19 g, 0.897 mmol), and 1-[3-(2-hydroxyethyl)-1H-indol-5-yl]cyclopropane-1-carboxylic acid (0.22 g, 0.897 mmol) according to General procedure A. The crude product was purified by column chromatography eluting with dichloromethane/EtOAc (100/0 to 70/30) and lyophilized to provide N-[cyclopropyl(2,4-dimethylphenyl)methyl]-1-[3-(2-hydroxyethyl)-1H-indol-5-yl]cyclopropane-1-carboxamide Ex.7a (0.242 g, 0.601 mmol) as an off-white solid.<br>Yield: 67%<br>mp: 67.4-79.2° C.<br>1H NMR (DMSO-d6): 0.03-0.13 (m, 2H), 0.27-0.41 (m, 2H), 0.94-1.11 (m, 3H), 1.26-1.37 (m, 2H), 2.19 (s, 3H), 2.20 (s, 3H), 2.83 (t, 2H, J = 7.38 Hz), 3.60-3.67 (m, 2H), 4.53 (t, 1H, J = 8.04 Hz), 4.61 (t, 1H, J = 5.4 Hz), 6.25 (d, 1H, J = 8.28 Hz), 6.88-6.91 (m, 2H), 7.03-7.06 (m, 2H), 7.16 (d, 1H, J = 2.22 Hz), 7.32 (d, 1H, J = 8.28 Hz), 7.49 (d, 1H, J = 1.47 Hz), 10.85 (d, 1H, J = 1.68 Hz).<br>m/z (ESI+): 403.3 (M + H)+, 425.3 (M + Na)+ (calc. mass: 402). |
| Ex.7 | dibenzyl 2-[5-(1-{[cyclopropyl(2,4-dimethylphenyl)methyl]carbamoyl}cyclopropyl)-1H-indol-3-yl]ethyl phosphate<br>From N-[cyclopropyl(2,4-dimethylphenyl)methyl]-1-[3-(2-hydroxyethyl)-1 H-indol-5-yl]cyclopropane-1-carboxamide Ex.7a (0.219 g, 0.544 mmol according to Protocole B1. The crude product was purified on successive chromatography columns with dichloromethane/EtOAc (7/3) and with dichloromethane/MeOH (100/0 to 90/10) to provide dibenzyl 2-[5-(1-{[cyclopropyl(2,4-dimethylphenyl)methyl]carbamoyl}cyclopropyl)-1H-indol-3-yl]ethyl phosphate Ex.7 (0.167 g, 0.252 mmol) as a colourless gum.<br>Yield: 46%<br>1H NMR (DMSO-d6): 0.02-0.10 (m, 2H), 0.24-0.36 (m, 2H), 0.96-1.04 (m, 3H), 1.24-1.37 (m, 2H), 2.18 (s, 6H), 3.01 (t, 2H, J = 6.69 Hz), 4.19 (q, 2H, J = 6.87 Hz), 4.50 (t, 1H, J = 8.19 Hz), 4.95 (dd, 4H, J = 8.1 Hz, J = 2.79 Hz), 6.27 (d, 1H, J = 8.28 Hz), 6.85-6.88 (m, 2H), 7.02 (d, 1H, J = 7.65 Hz), 7.07 (dd, 1H, J = 8.34 Hz, J = 1.65 Hz), 7.21 (d, 1H, J = 2.25 Hz), 7.28-7.38 (m, 11H), 7.52 (br(s), 1H), 10.97 (d, 1H, J = 2.13 Hz).<br>m/z (ESI+): 663.3 (M + H)+, 685.3 (M + Na)+ (calc. mass: 662). |

Intermediate Ex.8: Preparation of dibenzyl 2-{5-[1-({[4-methyl-2-(morpholin-4-yl)phenyl](phenyl) methyl}carbamoyl)cyclopropyl]-1H-indol-3-yl}ethyl phosphate

| Cpd. | Starting compounds, Reaction conditions and purification<br>Yield, MP, Appearance, ¹H NMR (solvent) data, Mass (ESI+ or ESI−) data |
|---|---|
| Ex.8a | carboxamide<br>From [4-methyl-2-(morpholin-4-yl)phenyl](phenyl)methanamine (protocol of synthesis disclosed by WO2018/138359) (0.3 g, 0.941 mmol), and 1-[3-(2-hydroxyethyl)-1H-indol-5-yl]cyclopropane-1-carboxylic acid (0.231 g, 0.941 mmol) according to General procedure A. The reaction was stirred at rt for 5 h. The crude solid was triturated successively with dichloromethane, EtOH, Et2O and hot MeOH, filtered and dried under high vacuum at 40° C. for 24 h to provide 1-[3-(2-hydroxyethyl)-1H-indol-5-yl]-N-{[4-methyl-2-(morpholin-4-yl)phenyl](phenyl)methyl}cyclopropane-1-carboxamide Ex.8a (0.087 g, 0.171 mmol) as a off-white solid.<br>Yield: 18%<br>mp: 240-248° C.<br>1H NMR (DMSO-d6): 1.01-1.10 (m, 2H), 1.34-1.5 (m, 2H), 1.95-2.04 (m, 2H), 2.08-2.28 (m, 2H), 2.24 (s, 3H), 2.69-2.86 (m, 6H), 3.54-3.71 (m, 2H), 4.63 (t, 1H, J = 5.4 Hz), 6.33 (d, 1H, J = 9.06 Hz), 6.91-6.97 (m, 2H), 7.01-7.06 (m, 3H), 7.11-7.27 (m, 6H), 7.36 (d, 1H, J = 8.31 Hz), 7.60 (br(s), 1H), 10.88 (br(s), 1H).<br>m/z (ESI+): 510.3 (M + H)+, 532.3 (M + Na)+ (calc, mass: 509). |
| Ex.8 | phosphate<br>From 1-[3-(2-hydroxyethyl)-1H-indol-5-yl]-N-{[4-methyl-2-(morpholin-4-yl)phenyl](phenyl)methyl}cyclopropane-1-carboxamide Ex.8a (0.067 g, 0.131 mmol) according to Protocol B1. The crude product was purified by column chromatography eluting with dichloromethane/EtOAc (7/3) to provide dibenzyl 2-{5-[1-({[4-methyl-2-(morpholin-4-yl)phenyl](phenyl)methyl}carbamoyl) cyclopropyl]-1H-indol-3-yl}ethyl phosphate Ex.8 (0.051 g, 0.066 mmol) as a colourless oil.<br>Yield: 50%<br>1H NMR (DMSO-d6): 0.99-1.09 (m, 2H), 1.31-1.50 (m, 2H), 1.96-2.18 (m, 4H), 2.22 (s, 3H), 2.69-2.87 (m, 4H), 2.98 (t, 2H, J = 6.93 Hz), 4.11-4.019 (m, 2H), 4.97 (d, 4H, J = 9.39 Hz), 6.34 (d, 1H, J = 9.51 Hz), 6.92-6.98 (m, 3H), 7.03-7.16 (m, 4H), 7.19-7.40 (m, 15H), 7.58 (br(s), 1H), 11.00 (d, 1H, J = 1.98 Hz).<br>m/z (ESI+): 770.4 (M + H)+, 792.4 (M + Na)+ (calc, mass: 769). |

Intermediate Ex.9: Preparation of dibenzyl 2-[5-(1-{[(dimethyl-1,2-oxazol-4-yl)(phenyl)methyl] carbamoyl}cyclopropyl)-1H-indol-3-yl]ethyl phosphate

| Cpd. | Starting compounds, Reaction conditions and purification<br>Yield, MP, Appearance, ¹H NMR (solvent) data, Mass (ESI+ or ESI−) data |
|---|---|
| Ex.9a | [(dimethyl-1,2-oxazol-4-yl)(phenyl)methyl][(2-methylpropane-2-sulfinyl)methylidene]amine<br>3,5-Dimethyl-1,2-oxazole-4-carbaldehyde (2.5 g, 20 mmol) was dissolved in dry THF. Titanium ethoxide (13.67 g, 60 mmol) and 2-methyl-2-propane-sulfinamide (2.42 g, 20 mmol) were added and the solution was stirred at room temperature for 48 h. Brine was added to quench the reaction and the mixture was stirred vigorously. EtOAc was added, the two layers were partitioned. The organic layer was dried over MgS04, filtered and concentrated under reduced pressure to afford [(dimethyl-1,2-oxazol-4-yl)(phenyl)methyl][(2-methylpropane-2-sulfinyl)methylidene]amine Ex.9a (3.95 g, 86%) as an oil. The compound was used as such for the next step. |
| Ex.9b | N-[(dimethyl-1,2-oxazol-4-yl)(phenyl)methyl]-2-methylpropane-2-sulfinamide<br>To [(dimethyl-1,2-oxazol-4-yl)(phenyl)methyl][(2-methylpropane-2-sulfinyl) methylidene]amine Ex.9a (3.951 g, 17 mmol) in dry THF was added a solution of phenylmagnesium bromide in THF (9.41 g, 52 mmol) at 0° C. The reaction mixture was stirred at room temperature for 24 h, quenched with water and extracted twice with EtOAc. Combined organic layer was washed twice with NH4Cl sol., brine, dried over MgSO4 and concentrated under reduced pressure. The crude was purified by column chromatography eluting with hexane/EtOAc (20/1 to 4/1) to afford N-[(dimethyl-1,2-oxazol-4-yl)(phenyl)methyl]-2-methylpropane-2-sulfinamide Ex.9b (4.03 g, 13 mmol). The product was directly engaged in the next step. |

| Cpd. | Starting compounds, Reaction conditions and purification Yield, MP, Appearance, ¹H NMR (solvent) data, Mass (ESI+ or ESI−) data |
|---|---|
| Ex.9c | (dimethyl-1,2-oxazol-4-yl)(phenyl)methanamine<br>N-[(dimethyl-1,2-oxazol-4-yl)(phenyl)methyl]-2-methylpropane-2-sulfinamide Ex.9b (2 g, 6.53 mmol) was solubilzed in 10 mL of 36% methanolic HCl. The reaction mixture was stirred at rt for 24 h and concentrated under reduced pressure. The residue was converted to the free amine and purified by column chromatography eluting with dichloromethane/EtOAc (12/1) and hexane/EtOAc/MeOH (1/1/0.1) to afford (dimethyl-1,2-oxazol-4-yl)(phenyl)methanamine Ex.9c (0.85 g, 4.2 mmol)<br>1H NMR (DMSO-d6): 2.01 (s, 3H); 2.16 (bs, 2H); 2.31 (s, 3H); 5.08 (s, 1H); 7.20-7.24 (m, 1H); 7.30-7.38 (m, 4H). |
| Ex.9d | N-[(dimethyl-1,2-oxazol-4-yl)(phenyl)methyl]-1-[3-(2-hydroxyethyl)-1H-indol-5-yl]cyclopropane-1-carboxamide<br>From (dimethyl-1,2-oxazol-4-yl)(phenyl)methanamine Ex.9c (0.2 g, 0.989 mmol), and 1-[3-(2-hydroxyethyl)-1H-indol-5-yl]cyclopropane-1-carboxylic acid (0.243 g, 0.989 mmol) according to General procedure A. The crude product was purified by column chromatography eluting with dichloromethane/MeOH (100 to 95/5) and lyophilized to provide N-[(dimethyl-1,2-oxazol-4-yl)(phenyl)methyl]-1-[3-(2-hydroxyethyl)-1H-indol-5-yl]cyclopropane-1-carboxamide Ex.9d (0.25 g, 0.582 mmol) as a white solid.<br>Yield: 58%<br>mp: 70-79° C.<br>1H NMR (DMSO-d6): 1.07-1.10 (m, 2H), 1.38-1.41 (m, 2H), 1.77 (s, 3H), 1.96 (s, 3H), 2.84 (t, 2H, J = 7.2 Hz), 3.63 (t, 2H, J = 7.2 Hz), 4.61 (br(s), 1H), 6.00 (d, 1H, J = 8.1 Hz), 6.84 (d, 1H, J = 8.1 Hz), 7.09-7.17 (m, 4H), 7.25-7.35 (m, 4H), 7.59 (d, 1H, J = 1.5 Hz), 10.84 (d, 1H, J = 1.8 Hz)<br>m/z (ESI+): 430.3 (M + H)+, 452.2 (M + Na)+, 881.6 (2M + Na)+ (calc. mass: 429). |
| Ex.9 | phosphate<br>From N-[(dimethyl-1,2-oxazol-4-yl)(phenyl)methyl]-1-[3-(2-hydroxyethyl)-1H-indol-5-yl]cyclopropane-1-carboxamide Ex.9d (0.2 g, 0.466 mmol) according to Protocol B1. The crude was purified by column chromatography eluting with dichloromethane/EtOAc (8/2) to provide dibenzyl 2-[5-(1-{(dimethyl-1,2-oxazol-4-yl)(phenyl)methyl]carbamoyl}cyclopropyl)-1H-indol-3-yl]ethyl phosphate Ex.9 (0.155 g, 0.225 mmol) as a white foam.<br>Yield: 48%<br>1H NMR (DMSO-d6): 1.05-1.08 (m, 2H), 1.37-1.40 (m, 2H), 1.76 (s, 3H), 1.94 (s, 3H), 3.01 (t, 2H, J = 6.9 Hz), 4.18 (q, 2H, J = 7.2 Hz), 4.94 (d, 2H, J = 1.8 Hz), 4.97 (d, 2H, J = 1.8 Hz), 5.99 (d, 1H, J = 8.1 Hz), 6.86 (d, 1H, J = 8.4 Hz), 7.09 (d, 2H, J = 7.5 Hz), 7.15 (dd, 1H, J = 8.4 Hz, J = 1.5 Hz), 7.20-7.38 (m, 15H), 7.59 (s, 1H), 10.96 (d, 1H, J = 1.8 Hz)<br>m/z (ESI+): 690.3 (M + H)+, 712.3 (M + Na)+ (calc. mass: 689). |

Example 2: Synthesis of Compounds According to the Invention

TABLE 1

| Cpd. | Starting compounds, Reaction conditions and purification Yield, MP, Appearance, ¹H NMR (solvent) data, Mass (ES+ or ES−) data |
|---|---|
| 1 {2-[5-(1-{(2,4-dimethylphenyl)(5-methylfuran-2-yl)methyl]carbamoyl}cyclopropyl)-1H-indol-3-yl]ethoxy}phosphonic acid | From Ex.1 (0.06 g, 0.085 mmol) in 5 mL of ethanol according to General procedure C.<br>Crude Cpd.1 was obtained as an oil which crystallized upon standing as a white solid (0.045 g, 0.086 mmol), quantitative yield.<br>1H NMR (DMSO-d6): 1.04-1.09 (m, 2H), 1.31-1.40 (m, 2H), 2.13 (s, 3H), 2.15 (s, 3H), 2.21 (s, 3H), 3.00 (t, 2H, J = 7.29 Hz), 4.03 (q, 2H, J = 7.05 Hz), −483017.00 (m, 1H), 5.88-5.93 (m, 1H), 6.09 (d, 1H, J = 8.19 Hz), 6.72 (d, 1H, J = 8.4 Hz), 6.80 (d, 1H, J = 8.25 Hz), 6.89-6.94 (m, 1H), 6.94-6.97 (m, 1H), 7.10 (dd, 1H, J = 8.64 Hz, J = 1.95 Hz), 7.23 (d, 1H, J = 2.37 Hz), 7.34 (dd, 1H, J = 8.52 Hz, J = 0.39 Hz), 7.56 (d, 1H, J = 1.11 Hz), 10.91 (m, 1H); m/z (ESI+): 545 (M + Na)+ (calc. mass: 522) |
| 2 disodium 2-[5-(1-{(2,4-dimethylphenyl)(5-methylfuran-2-yl)methyl]carbamoyl} | From Cpd.1 (0.045 g, 0.086 mmol) in methanol (2mL) according to General procedure D to afford Cpd.2 as a white solid (0.048 g, 0.082 mmol), yield: 38%, mp: 176-179° C.<br>1H NMR (DMSO d6): 0.71-1.03 (m, 2H), 1.12-1.34 (m, 2H), 1.79-2.38 (m, 9H), 2.74-3.02 (m, 2H), 3.73-4.14 (m, 2H), |

TABLE 1-continued

| Cpd. | Starting compounds, Reaction conditions and purification Yield, MP, Appearance, ¹H NMR (solvent) data, Mass (ES+ or ES−) data | |
|---|---|---|
| | cyclopropyl)-1H-indol-3-yl] ethyl phosphate | 5.53-5.89 (m, 2H), 5.97-6.12 (m, 1H), 6.47-7.68 (m, 8H), 10.94 (br(s), 1H); m/z (ESI+): 545 (M + Na)+ (calc, mass: 522) |
| 3 | {2-[5-(1-{[(2-methoxy-4-methylphenyl)(phenyl)methyl]carbamoyl}cyclopropyl)-1H-indol-3-yl]ethoxy} phosphonic acid | From Ex.2 (0.1 g, 0.14 mmol) according to General procedure C to provide Cpd.3 as a white solid (0.05 g, 0.094 mmol), yield: 67%, mp: 122-132° C. 1H NMR (DMSO-d6): 1.03-1.14 (m, 2H), 1.32-1.46 (m, 2H), 2.20 (s, 3H), 2.94 (s, 3H), 3.03 (t, 2H, J = 7.2 Hz), 4.02-4.11 (m, 2H), 6.02 (d, 1H, J = 9.3 Hz), 6.62 (s, 1H), 6.68 (d, 1H, J = 7.5 Hz), 7.02 (d, 2H, J = 7.5 Hz), 7.09-7.27 (m, 7H), 7.42 (d, 1H, J = 8.4 Hz), 7.63 (s, 1H), 10.90 (br(s), 2H), 10.98 (d, 1H, J = 2.1 Hz); m/z (ESI+): 535.2 (M + H)+, 557.3 (M + Na)+, 1069.5 (2M + H)+, 1091.4 (2M + Na)+ (calc, mass: 534). |
| 4 | disodium 2-[5-(1-{[(2-methoxy-4-methylphenyl)(phenyl)methyl]carbamoyl}cyclopropyl)-1H-indol-3-yl] ethyl phosphate | From Cpd.3 (0.048 g, 0.09 mmol) according to General procedure D. The mixture was diluted with water and lyophilized to provide Cpd.4 as a white foam (0.048 g, 0.083 mmol), yield: 92%, mp: 228.1-238.1° C. 1H NMR (D2O): 1.26-1.34 (m, 2H), 1.49-1.61 (m, 2H), 2.24 (s, 3H), 2.87 (s, 3H), 3.05 (t, 2H, J = 7.26 Hz), 4.03 (q, 2H, J = 7.2 Hz), 6.02 (s, 1H), 6.64 (s, 1H), 6.77 (d, 1H, J = 7.59 Hz), 7.10-7.17 (m, 3H), 7.19-7.32 (m, 4H), 7.36 (s, 1H), 7.48 (d, 1H, J = 8.4 Hz), 7.86 (d, 1H, J = 1.08 Hz); m/z (ESI+): 535.3 (M + H)+, 557.2 (M + Na)+ (calc, mass: 578). |
| 5 | {2-[5-(1-{[(2,4-dimethylphenyl)(6-methyl pyridin-2-yl)methyl]carbamoyl}cyclopropyl)-1H-indol-3-yl]ethoxy} phosphonic acid | From Ex.3 (0.227 g, 0.318 mmol) according to General procedure C to provide Cpd.5 as a white foam (0.154 g, 0.289 mmol), yield 90%, mp: 151-164° C. 1H NMR (DMSO-d6): 1.01-1.07 (m, 2H), 1.30-1.35 (m, 2H), 2.01 (s, 3H), 2.17 (s, 3H), 2.30 (s, 3H), 3.03 (t, 2H, J = 7.5 Hz), 4.01-4.09 (m, 2H), 5.95 (d, 1H, J = 6.6 Hz), 6.73 (d, 1H, J = 7.8 Hz), 6.84-6.90 (m, 3H), 6.99 (d, 1H, J = 7.8 Hz), 7.15 (dd, 1H, J = 8.4 Hz, J = 1.8 Hz), 7.27 (d, 1H, J = 2.4 Hz), 7.42 (d, 1H, J = 8.4 Hz), 7.51 (t, 1H, J = 7.5 Hz), 7.61 (s, 1H), 7.72 (d, 1H, J = 6.6 Hz), 10.97 (d, 1H, J = 2.1 Hz), 11.00 (br(s), 2H) ; m/z (ESI+): 534.3 (M + H)+, 556.3 (M + Na)+ (calc, mass: 533). |
| 6 | disodium {2-[5-(1-{[(2,4-dimethyl phenyl)(6-methyl pyridin-2-yl)methyl]carbamoyl}cyclopropyl)-1H-indol-3-yl]ethoxy} phosphonic acid | From Cpd.5 (0.15 g, 0.28 mmol) according to General procedure D to provide Cpd.6 as a white foam (0.153 g, 0.265 mmol), yield: 94%, mp: 208-228° C. 1H NMR (D2O): 1.21-1.31 (m, 2H), 1.45-1.52 (m, 2H), 2.16 (s, 3H), 2.20 (s, 3H), 2.27 (s, 3H), 3.02 (t, 2H, J = 7.2 Hz), 4.00 (q, 2H, J = 7.2 Hz), 6.04 (s, 1H), 6.54 (d, 1H, J = 8.1 Hz), 6.78 (d, 1H, J = 7.5 Hz), 6.92 (d, 1H, J = 8.1 Hz), 7.02 (s, 1H), 7.09 (d, 1H, J = 7.8 Hz), 7.27-7.31 H (m, 2H), 7.42 (d, 1H, J = 8.4 Hz), 7.55 (t, 1H, J = 7.5 Hz), 7.83 (d, 1H, J = 1.2 Hz), m/z (ESI+): 534.3 (M + H)+, 556.2 (M + Na)+ (calc, mass: 577). |
| 7 | {2-[5-(1-{[(3-chlorophenyl)(2,4-dimethyl phenyl)methyl]carbamoyl}cyclopropyl)-1H-indol-3-yl]ethoxy} phosphonic acid | From Ex.4 (0.1 g, 0.136 mmol) according to General procedure C to afford Cpd.7 as a beige solid (0.069 g, 0.125 mmol), yield: 91%, mp: 94.5-124.3° C. 1H NMR (DMSO-d6): 1.06-1.10 (m, 2H), 1.34-1.38 (m, 2H), 2.13 (s, 3H), 2.21 (s, 3H), 3.00 (t, 2H, J = 7.26 Hz), 4.04 (q, 2H, J = 14.76 Hz, J = 7.35 Hz), 6.20 (d, 1H, J = 8.28 Hz), 6.71 (d, 1H, J = 7.83 Hz), 6.89 (d, 1H, J = 8.16 Hz), 6.96-6.99 (m, 2H), 7.04-7.06 (m, 2H), 7.12 (dd, 1H, J = 8.37 Hz, J = 1.62 Hz), 7.21 (d, 1H, J = 2.25 Hz), 7.26-7.36 (m, 3H), 7.56 (br(s), 1H), 10.90 (m, 2H, J = 2.01 Hz), m/z (ESI+) : 553.2 (M + H)+, 575.2 (M + Na)+ (calc. mass: 552). |
| 8 | disodium 2-[5-(1-{[(3-chloro phenyl)(2,4-dimethylphenyl)methyl]carbamoyl}cyclopropyl)-1H-indol-3-yl]ethyl phosphate | From Cpd.7 (0.068 g, 0.123 mmol) according to General procedure D to afford Cpd.8 as a white foam (0.065 g, 0.109 mmol), yield: 88%, mp: 219.6-229.2° C. 1H NMR (D2O): 1.24-1.28 (m, 2H), 1.49-1.53 (m, 2H), 2.11 (s, 3H), 2.12 (s, 3H), 3.02 (t, 2H, J = 7.02 Hz), 3.99 (q, 2H, J = 7.05 Hz), 6.12 (s, 1H), 6.60 (d, 1H, J = 7.98 Hz), 6.73 (d, 1H, J = 7.89 Hz), 6.93-7.02 (m, 3H), 7.19-7.37 (m, 5H), 7.81 (d, 1H, J = 0.9 Hz), m/z (ESI+): 553.2 (M + H)+, 575.2 (M + Na)+ (calc. mass: 596). |
| 9 | {2-[5-(1-{[(4 methoxy-2-methylphenyl) | From Ex.5 (0.246 g, 0.344 mmol) according to General procedure C to provide Cpd.9 as a beige solid (0.152 g, 0.284 mmol), yield: 82%, mp: 110.2-127.9° C. |

TABLE 1-continued

| Cpd. | | Starting compounds, Reaction conditions and purification Yield, MP, Appearance, $^1$H NMR (solvent) data, Mass (ES+ or ES−) data |
|---|---|---|
| | (phenyl)methyl] carbamoyl} cyclopropyl)- 1H-indol-3- yl]ethoxy} phosphonic acid | 1H NMR (DMSO-d6): 1.05-1.09 (m, 2H), 1.32-1.38 (m, 2H), 2.13 (s, 3H), 3.01 (t, 2H, J = 7.26 Hz), 3.69 (s, 3H), 4.05 (q, 2H, J = 7.26 Hz), 6.15 (d, 1H, J = 8.16 Hz), 6.62-6.75 (m, 4H), 7.02-7.05 (m, 2H), 7.13 (dd, 1H, J = 8.4 Hz, J = 1.56 Hz), 7.17-7.34 (m, 5H), 7.59 (br(s), 1H), 10.92 (m, 2H), m/z (ESI+) : 535.2 (M + H)+, 557.2 (M + Na)+ (calc. mass: 534). |
| 10 | disodium 2-[5- (1-{(4-methoxy- 2-methylphenyl) (phenyl)methyl] carbamoyl} cyclopropyl)- 1H-indol-3-yl] ethyl phosphate | From Cpd.9 (0.144 g, 0.269 mmol) according to General procedure to provide Cpd.10 as a white foam (0.149 g, 0.258 mmol), yield: 95%, mp: 214.1-230.9° C. 1H NMR (D2O): 1.24-1.27 (m, 2H), 1.51-1.52 (m, 2H), 2.16 (s, 3H), 3.01 (t, 2H, J = 7.35 Hz), 3.63 (s, 3H), 4.00 (q, 2H, J = 7.29 Hz), 6.12 (s, 1H), 6.36 (dd, 1H, J = 8.55 Hz, J = 2.85 Hz), 6.61 (d, 1H, J = 8.82 Hz), 6.73 (d, 1H, J = 2.61 Hz), 7.07-7.10 (m, 2H), 7.22-7.35 (m, 6H), 7.81 (d, 1H, J = 1.05 Hz), m/z (ESI+): 535.2 (M + H)+, 557.3 (M + Na)+ (calc. mass: 578). |
| 11 | {2-[5-(1-{[(4 methoxy-2- (pyrrolidin-1- yl)phenyl] (phenyl)methyl} carbamoyl) cyclopropyl]- 1H-indol-3-yl} ethoxy) phosphonic acid | From Ex.6 (0.083 g, 0.108 mmol) according to General procedure C to provide Cpd.11 as a beige solid (0.047 g, 0.08 mmol), yield: 73%, mp: 130.6-141.1° C. 1H NMR (DMSO-d6): 1.01-1.18 (m, 4H), 1.22-1.50 (m, 4H), 2.11-2.18 (m, 2H), 2.34-2.41 (m, 2H), 3.02 (t, 2H, J = 7.35 Hz), 3.67 (s, 3H), 4.00-4.09 (m, 2H), 6.22 (d, 1H, J = 8.76 Hz), 6.56-6.59 (m, 2H), 7.02-.707 (m, 3H), 7.12-7.19 (m, 3H), 7.27-7.29 (m, 3H), 7.37 (d, 1H, J = 8.4 Hz), 7.64 (br(s), 1H), 10.95 (d, 2H, J = 1.95 Hz), m/z (ESI+): 590.3 (M + H)+, 612.3 (M + Na)+ (calc. mass: 589). |
| 12 | disodium 2-{5- [1-({[4-methoxy- 2-(pyrrolidin-1- yl)phenyl] (phenyl)methyl} carbamoyl) cyclopropyl]- 1H-indol-3-yl} ethyl phosphate | From Cpd.11 (0.04 g, 0.068 mmol) according to General procedure D to provide Cpd.12 as a white foam (0.038 g, 0.06 mmol), yield: 88%, mp: 222.1-234.6° C. 1H NMR (D2O): 1.14-1.20 (m, 2H), 1.35-1.52 (m, 6H), 2.35-2.42 (m, 2H), 2.55-2.60 (m, 2H), 2.93 (t, 2H, J = 7.05 Hz), 3.54 (s, 3H), 3.91 (q, 2H, J = 7.2 Hz), 6.11 (s, 1H), 6.24 (dd, 1H, J = 8.67 Hz, J = 2.55 Hz), 6.50 (d, 1H, J = 2.55 Hz), 6.73 (d, 1H, J = 8.61 Hz), 7.04 (d, 2H, J = 7.26 Hz), 7.12-7.28 (m, 6H), 7.74 (d, 1H, J = 1.05 Hz), m/z (ESI+): 590.3 (M + H)+, 612.3 (M + Na)+ (calc. mass: 633). |
| 13 | {2-[5-(1- {[cyclopropyl (2,4-dimethyl phenyl)methyl] carbamoyl} cyclopropyl)- 1H-indol-3-yl] ethoxy} phosphonic acid | From Ex.7 (0.167 g, 0.252 mmol) according to General procedure C to provide Cpd.13 as an off-white solid (0.105 g, 0.218 mmol), yield: 86%, mp: 95.4-119.1° C. 1H NMR (DMSO-d6): 0.01-0.16 (m, 2H), 0.26-0.42 (m, 2H), 0.96-1.12 (m, 3H), 1.26-1.35 (m, 2H), 2.19 (s, 3H), 2.20 (s, 3H), 3.01 (t, 2H, J = 7.08 Hz), 4.05 (q, 2H, J = 7.41 Hz), 4.51 (t, 1H, J = 8.01 Hz), 6.30 (d, 1H, J = 8.25 Hz), 6.89-6.91 (m, 2H), 7.04-7.08 (m, 2H), 7.23 (d, 1H, J = 2.22 Hz), 7.34 (d, 1H, J = 8.28 Hz), 7.52 (br(s), 1H), 10.93 (dd, 2H, J = 1.95 Hz), m/z (ESI+): 483.2 (M + H)+, 505.2 (M + Na)+ (calc. mass: 482). |
| 14 | disodium 2-[5- (1-{[cyclopropyl (2,4-dimethyl phenyl)methyl] carbamoyl} cyclopropyl)- 1H-indol-3-yl] ethyl phosphate | From Cpd.13 (0.089 g, 0.185 mmol) according to General procedure D to provide Cpd.14 as a yellow solid (0.096 g, 0.182 mmol), yield: 98%, mp: 230-238° C. 1H NMR (D2O): 0.12-0.16 (m, 2H), 0.35-0.45 (m, 2H), 1.02-1.08 (m, 1H), 1.14-1.28 (m, 2H), 1.35-1.48 (m, 2H), 2.24 (s, 6H), 3.06 (t, 2H, J = 7.2 Hz), 4.02 (q, 2H, J = 7.2 Hz), 4.47 (d, 1H, J = 908.1 Hz), 6.99-7.04 (m, 2H), 7.12 (d, 1H, J = 7.8 Hz), 7.24 (dd, 1H, J = 8.4 Hz, J = 1.8 Hz), 7.36 (s, 1H), 7.47 (dd, 1H, J = 8.4 Hz, J = 0.3 Hz), 7.79-7.80 (m, 1H), m/z (ESI+): 483.3 (M + H)+, 505.2 (M + Na)+, 965.4 (2M + H)+, 987.5 (2M + Na)+ (calc. mass: 526). |
| 15 | {2-[5-(1-{[(4 methyl-2- (morpholin-4-yl) phenyl]phenyl) methyl} carbamoyl) cyclopropyl]- 1H-indol-3-yl} ethoxy) phosphonic acid | From Ex.8 (0.051 g, 0.066 mmol) according to General procedure C to provide Cpd.15 as an off-white solid (0.031 g, 0.053 mmol), yield: 79%, mp: 141.6-163.5° C. 1H NMR (DMSO-d6): 1.03-1.12 (m, 2H), 1.31-1.49 (m, 2H), 1.96-2.06 (m, 2H), 2.11-2.28 (m, 2H), 2.24 (s, 3H), 2.72-2.91 (m, 4H), 3.01 (t, 2H, J = 7.14 Hz), 3.97-4.09 (m, 2H), 6.33 (d, 1H, J = 8.94 Hz), 6.93-7.28 (m, 11H), 7.38 (d, 1H, J = 8.37 Hz), 7.63 (br(s), 1H), 10.96 (d, 2H, J = 1.62 Hz), m/z: Mass Electrospray Ionisation (ESI+): 590.3 (M + H)+, 612.3 (M + Na)+ (calc. mass: 589). |
| 16 | disodium 2-{5- [1-({[4-methyl-2- (morpholin-4-yl) | From Cpd.15 (0.03 g, 0.052 mmol) according to General procedure D to provide Cpd.16 as a white foam (0.029 g, 0.046 mmol), yield: 88%, mp: 216-219° C. |

TABLE 1-continued

| Cpd. | | Starting compounds, Reaction conditions and purification Yield, MP, Appearance, $^1$H NMR (solvent) data, Mass (ES+ or ES−) data |
|---|---|---|
| | phenyl]phenyl)methyl}carbamoyl)cyclopropyl]-1H-indol-3-yl}ethyl phosphate | 1H NMR (D2O): 1.17-1.37 (m, 2H), 1.45-1.63 (m, 2H), 1.98-2.19 (m, 4H), 2.24 (s, 3H), 2.76-2.92 (m, 2H), 2.93-2.99 (m, 2H), 3.03 (t, 2H, J = 7.5 Hz), 4.01 (q, 2H, J = 6.3 Hz), 6.33 (s, 1H), 7.02 (d, 1H, J = 7.5 Hz), 7.09 (s, 1H),-691211.00 (m, 2H), 7.18-7.25 (m, 2H), 7.27-7.32 (m, 3H), 7.34 (s, 1H), 7.43 (d, 1H, J = 8.1 Hz), 7.86 (d, 1H, J = 0.9 Hz), m/z (ESI+): 590.3 (M + H)+, 612.4 (M + Na)+ (calc. mass: 633) |
| 17 | {2-[5-(1-{[(dimethyl-1,2-oxazol-4-yl)(phenyl)methyl]carbamoyl}cyclopropyl)-1H-indol-3-yl]ethoxy}phosphonic acid | From Ex. 9 (0.14 g, 0.203 mmol) according to General procedure C to afford Cpd.17 as a white foam (0.093 g, 0.183 mmol), yield: 90%, mp: 109-120° C. 1H NMR (DMSO-d6): 1.08-1.15 (m, 2H), 1.38-1.41 (m, 2H), 1.78 (s, 3H), 1.96 (s, 3H), 3.01 (t, 2H, J = 6.9 Hz), 4.04 (q, 2H, J = 7.2 Hz), 5.99 (d, 1H, J = 8.1 Hz), 6.88 (d, 1H, J = 8.1 Hz), 7.09-7.16 (m, 3H), 7.22-7.26 (m, 2H), 7.30-7.36 (m, 3H), 7.61 (s, 1H), 10.92 (d, 1H, J = 2.1 Hz), 11.00 (br(s), 2H), m/z (ESI+): 510.2 (M + H)+, 532.2 (M + Na)+, 1019.5 (2M + H)+, 1041.5 (2M + Na)+ (calc, mass: 509). |
| 18 | disodium 2-[5-(1-{[(dimethyl-1,2-oxazol-4-yl)(phenyl)methyl]carbamoyl}cyclopropyl)-1H-indol-3-yl]ethyl phosphate | From Cpd.17 (0.088 g, 0.173 mmol) according to Genral procedure D to provide Cpd.18 as a pale yellow foam (0.091 g, 0.164 mmol), yield: 95%, mp: 220-243° C. 1H NMR (D2O): 1.28-1.32 (m, 2H), 1.52-1.55 (m, 2H), 1.89 (s, 3H), 1.96 (s, 3H), 3.04 (t, 2H, J = 7.2 Hz), 4.00 (q, 2H, J = 7.5 Hz), 5.89 (s, 1H), 7.14-7.17 (m, 2H), 7.30-7.37 (m, 5H), 7.46 (dd, 1H, J = 8.4 Hz, J = 0.6 Hz), 7.86-7.87 (m, 1H), m/z (ESI+): 510.2 (M + H)+, 532.2 (M + Na)+, 1019.5 (2M + H)+, 1041.5 (2M + Na)+ (calc, mass: 553). |

Example 3: Solubility of Compounds According to the Invention

General procedure: The test compound was solubilized in phosphate buffer pH=7.4 at a given concentration (test concentration). The mixture was maintained under vigorous stirring for 24 hours at room temperature. In case a insoluble solid appeared, it was removed by centrifugation and the concentration of the test compound in the solution was determined by LC-MS/MS using appropriate methods.

| Test compound | Solubility | Solubility ratio |
|---|---|---|
| Cpd.2 | 143 mg/mL | Cpd.2/Cpd.A |
| Cpd.A | 0.09 mg/mL | 1 588 |
| Cpd.4 | 11.20 mg/mL | Cpd.4/Ex.2a |
| Ex.2a | 0.0016 mg/mL | 7 000 |
| Cpd.6 | >62.70 mg/mL | Cpd.6/Ex.3a |
| Ex.3a | 0.0052 mg/mL | ≥12 000 |
| Cpd.8 | >10.00 mg/mL | Cpd.8/Ex.4a |
| Ex.4a | 0.0001 mg/mL | ≥100 000 |
| Cpd.10 | >50.37 mg/mL | Cpd.10/Ex.5a |
| Ex.5a | 0.0037 mg/mL | ≥13513 |
| Cpd.14 | >70.79 mg/mL | Cpd.14/Ex.7a |
| Ex.7a | 0.0119 mg/mL | ≥5 949 |
| Cpd.16 | 3.64 mg/mL | Cpd.16/Ex.8a |
| Ex.8a | 0.00007 mg/mL | 52 057 |
| Cpd.18 | >71.35 mg/mL | Cpd.18/Ex.9d |
| Ex.9d | 0.0783 mg/mL | ≥911 |

The compounds according to the invention show a better solubility than their unphosphated counterpart. For example, Cpd.2 is at least 1500 fold more soluble when compared to its unphosphated analogue Cpd. A, and Cpd.8 is more than 100 000 fold more soluble when compared to its unphosphated analogue Ex.4a.

Example 4: Stability of Compounds According to the Invention in Water

General procedure: compound 2 (Cpd. 2) according to the invention was dissolved in water in order to obtain a 5 mg/mL concentration. The solution was stirred for 7 days at room temperature. Compound 2 was quantified at different time points (0, 5 days and 7 days) by UPLC/MS using appropriate method.

Results are expressed as percentage of initial signal area for Cpd.2 (time point (1-day).

The stability at room temperature of Cpd.2 at different times is reported in the table below.

| Compound 2 stability in water | |
|---|---|
| Time point (days) | Cpd.2 5 mg/mL |
| 0 | 100% |
| 5 | 98% |
| 7 | 98% |

These results show that compounds according to the invention are highly stable in water.

Example 5: Metabolic Stability of Compounds According to the Invention in Bronchoalveolar Lavage Fluid (Balf)

General procedure: human bronchoalveolar lavage fluid (hBALf) was purchased from BiolVT. Sample was collected from an individual donor. The only known information provided for the donor were age and gender. Information regarding the health status of the donor was not known.

Figure 2:
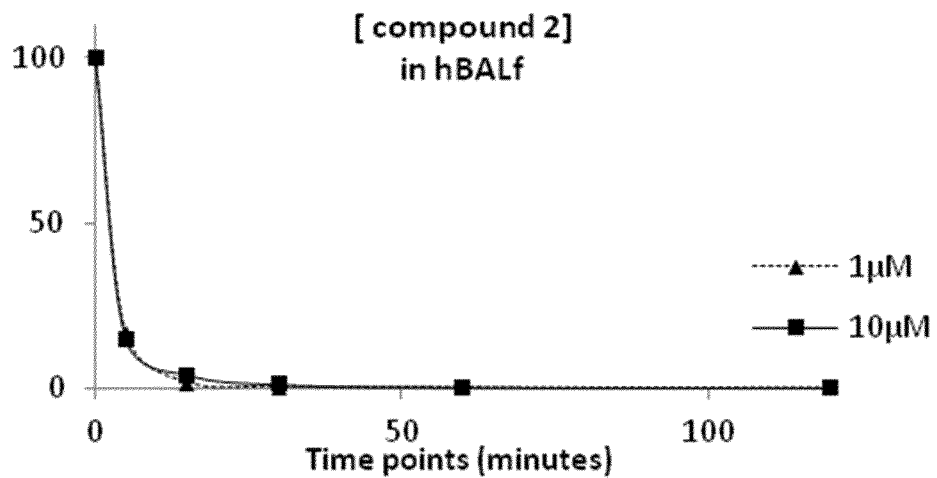
FIG. 2: Metabolic stability of Cpd. 2 in bronchoalveolar lavage fluid (Balf)

The hydrolysis of compound 2 was tested at the concentration of 1 μM and 10 μM for 120 minutes (time points 5, 15, 30, 60 and 120 minutes). Quantification of the compound was then carried out by LC-MS/MS using appropriate methods. Results were expressed as percentage of initial signal area (time point (1-min) as shown in FIG. 2.

The quantification of Cpd.2 in hBALf is reported in the table below.

| Cpd.2 quantification in hBALf at 1 and 10 μM | | |
|---|---|---|
| Time point (min) | Cpd.2 1 μM | Cpd.2 10 μM |
| 0 | 100% | 100% |
| 5 | 16.46% | 14.98% |
| 15 | 1.84% | 4.27% |
| 30 | 0.57% | 1.38% |
| 60 | 0.28% | 0.49% |
| 120 | 0.19% | 0.25% |

These results show that compounds according to the invention are rapidly hydrolyzed in biological fluids.

Example 6: In Vivo Absorption Study after Nasal Instillation

All the experiments were conducted in Artimmune laboratory by authorized technicians regularly employed by the company and directed by a scientist of Artimmune. Manipulation of animals was conducted carefully in order to reduce stress at the minimum. All the experiments were performed in compliance with the guidelines of French Ministry of Agriculture for experiments with laboratory animals (law 87-848). The study was conducted in compliance with Animal Health Regulation (Council directive No. 2010/63/UE and, French decree no. 2013-118 of Feb. 1 2013 on protection of animals), and in accordance with the Artimmune/CNRS facility accreditation for experimentation (no D45-234-6), for OVA induced inflammation model project accreditation for experimentation (CLE-CECCO-1085-Procedure 2).

General procedure: BALB/cByJ female mice at 8 weeks of age (ten groups of animals and one group control, three animals per group) were used to determine the concentrations of compounds according to the invention in lung. The compounds administered to the mice were solubilized in an aqueous solution of NaCl 0.9% to reach target concentrations of 0.1 and 2 mg/mL. 20 μL of compound solution were administered by intranasal route to animals.

Following administration of the compounds, heart was perfused to remove circulating test compounds before lung collection. Lungs were sampled over 2 h time-course (5 min, 15 min, 60 min and 2 h00).

Dephosphated compounds following metabolisation were quantified by LC-MS/MS in lungs using appropriate methods.

Figure 3A:
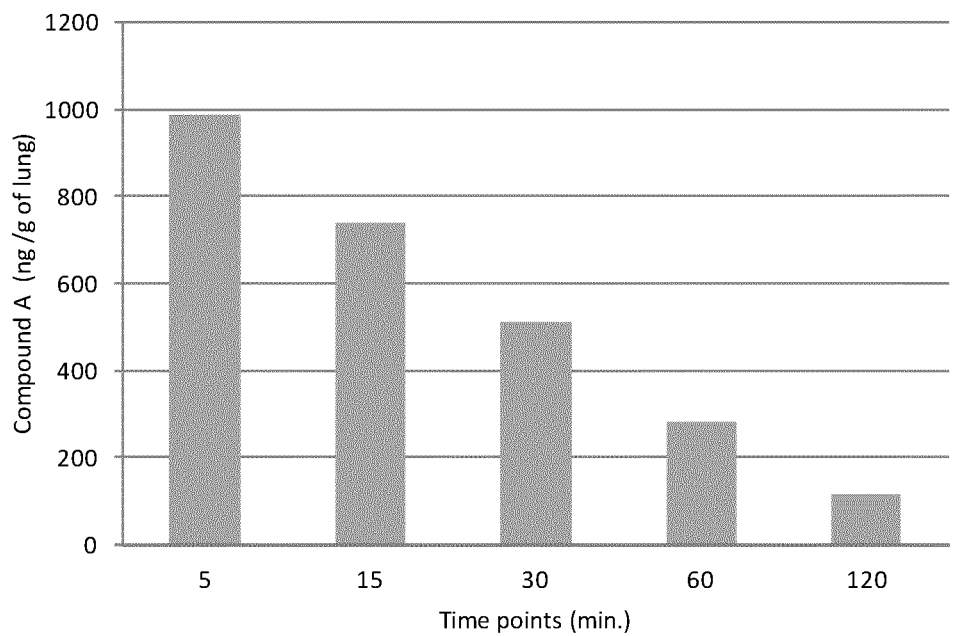
FIG. 3: In vivo absorption study of Cpd. 2 (FIGS. 3C and 3D) and its dephosphated derivative Cpd. A (FIGS. 3A and 3B) in lung tissue after nasal instillation of Cp.2 at 0.1 mg/kg (FIGS. 3A and 3C) and 2.0 mg/kg (FIGS. 3B and 3D).
Figure 3B:
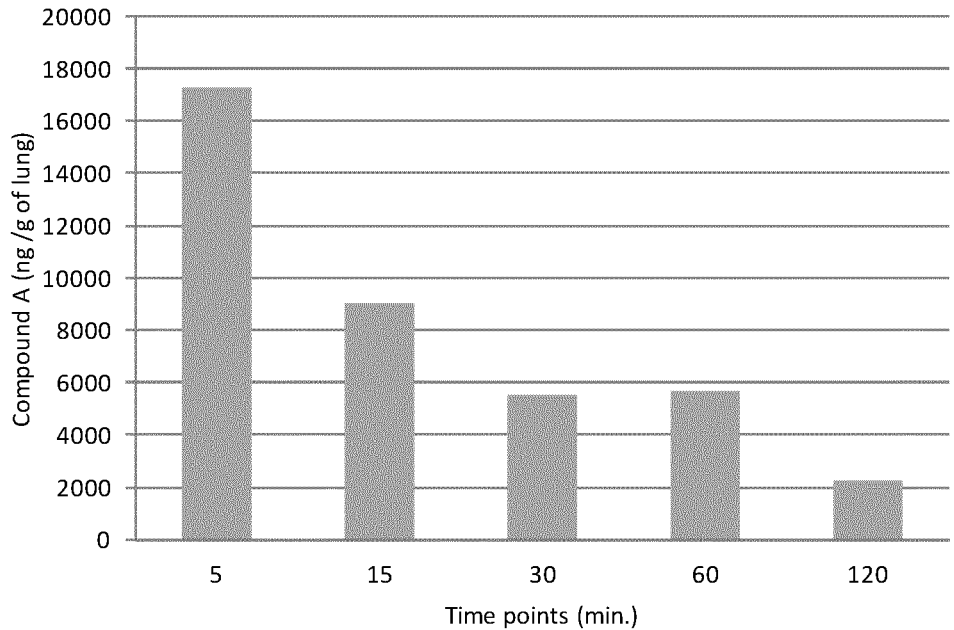

FIGS. 3a and 3b show absorption of dephosphated derivative (Cpd.A) after nasal instillation of Cpd.2 in BALB/cByJ female mice at 0.1 mpk and 2 mpk respectively.

Figure 3C:
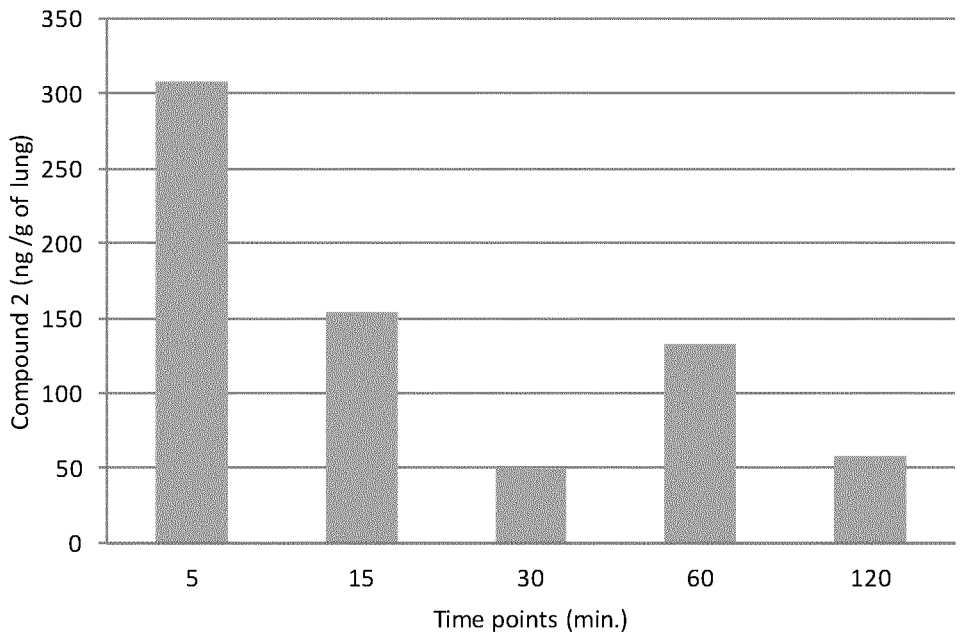
Figure 3D:
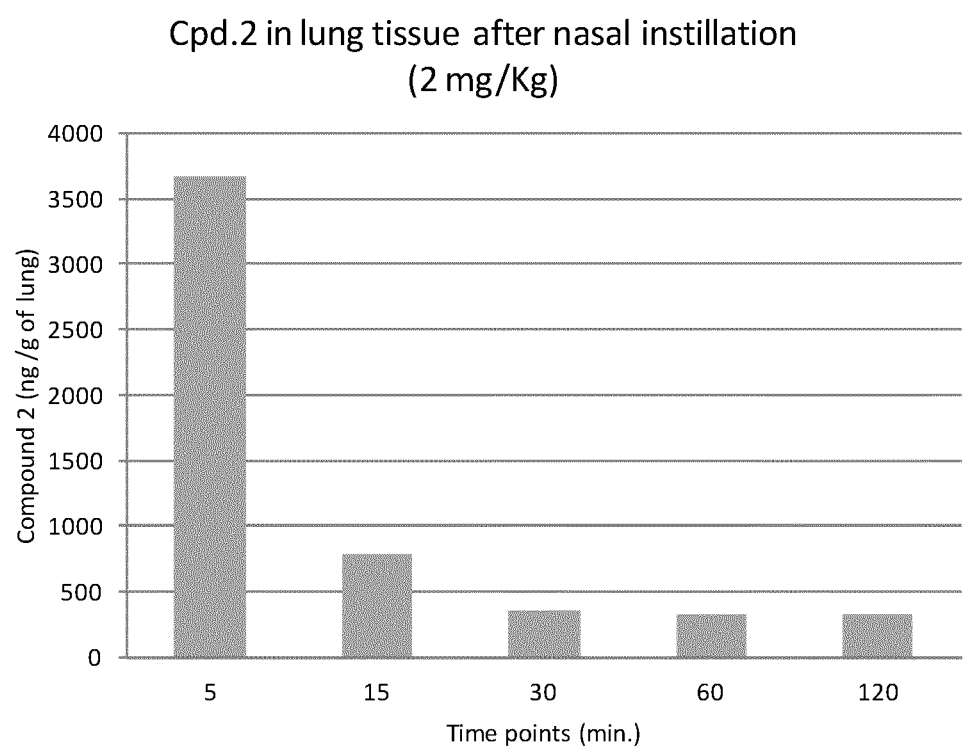

In the same manner, FIGS. 3c and 3d show quantification of Cpd.2 in lung after nasal instillation in BALB/cByJ female mice at 0.1 mpk and 2 mpk respectively.

The results show that the compounds of formula (I) according to the invention are rapidly hydrolyzed in vivo and allow absorption of the active compound in the lung.

The invention claimed is:

1. A compound having the following formula (I):

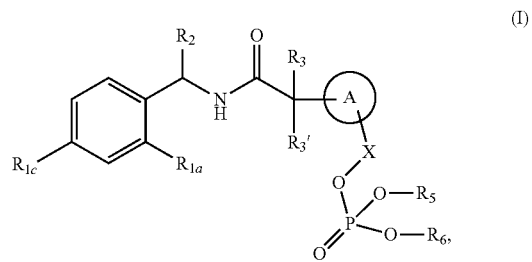

or a stereoisomer or a pharmaceutically acceptable salt thereof
wherein:
A is a ring of the following formula (a):

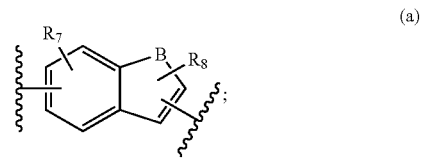

in which:
B represents a NH group; an oxygen atom; or a $SO_2$ group,
$R_7$ represents a hydrogen, a halogen, or a ($C_1$-$C_6$) alkyloxy group, and
$R_8$ represents a hydrogen or a ($C_1$-$C_6$)alkyl group,
$R_{1a}$ and $R_{1c}$ represent independently a hydrogen, a ($C_1$-$C_6$)alkyl group, a ($C_1$-$C_6$)alkyloxy group, a halogen, or a heterocycloalkyl optionally substituted by a ($C_1$-$C_6$)alkyl group;
$R_2$ represents a ($C_1$-$C_6$)alkyl group or a ring selected from the group consisting of a cycloalkyl, a heterocycloalkyl, an aryl, and a heteroaryl, said ring being optionally substituted by at least one radical selected from the group consisting of a ($C_1$-$C_6$)alkyl group, and a halogen;
$R_3$ and $R_{3'}$ represent independently a hydrogen or a ($C_1$-$C_6$)alkyl group, or
$R_3$ and $R_{3'}$ may form together, with the carbon atom to which they are attached, a cycloalkyl;
X represents a ($C_1$-$C_6$)alkyl group; and
$R_5$ and $R_6$ represent independently a hydrogen or a ($C_1$-$C_6$)alkyl group.

2. The compound according to claim 1, wherein A has the following formulae ($a_1$) or ($a_2$).

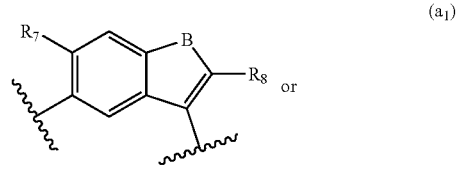

-continued

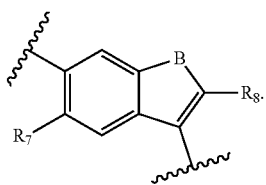
(a₂)

3. The compound according to claim 1, wherein B is a NH group.

4. The compound according to claim 1, wherein:
$R_{1a}$ represents a ($C_1$-$C_6$)alkyl group, a ($C_1$-$C_6$)alkyloxy group, a halogen, or a heterocycloalkyl; and
$R_{1c}$ represents a hydrogen, a ($C_1$-$C_6$)alkyl group, a ($C_1$-$C_6$)alkyloxy group, or a halogen.

5. The compound according to claim 1, wherein $R_2$ represents a heteroaryl, said heteroaryl being optionally substituted by at least one radical selected from the group consisting of a ($C_1$-$C_6$)alkyl group and a halogen.

6. The compound according to claim 1, wherein $R_5$ and $R_6$ represent a hydrogen.

7. The compound according to claim 1, wherein X is a linear ($C_1$-$C_6$)alkyl group.

8. The compound according to claim 1, wherein the pharmaceutically acceptable salt of the compound of formula (I) is a sodium salt, a potassium salt, or a calcium salt.

9. The compound according to claim 1, wherein said compound is selected from the group consisting of:
{2-[5-(1-{[(2,4-dimethylphenyl)(5-methylfuran-2-yl) methyl]carbamoyl}cyclopropyl)-1H-indol-3-yl] ethoxy}phosphonic acid;
disodium 2-[5-(1-{[(2,4-dimethylphenyl)(5-methylfuran-2-yl)methyl]carbamoyl}cyclopropyl)-1H-indol-3-yl] ethyl phosphate;
{2-[5-(1-{[(2-methoxy-4-methylphenyl)(phenyl)methyl] carbamoyl}cyclopropyl)-1H-indol-3-yl] ethoxy}phosphonic acid;
disodium 2-[5-(1-{[(2-methoxy-4-methylphenyl)(phenyl) methyl]carbamoyl}cyclopropyl)-1H-indol-3-yl]ethyl phosphate;
{2-[5-(1-{[(2,4-dimethylphenyl)(6-methyl pyridin-2-yl) methyl]carbamoyl}cyclopropyl)-1H-indol-3-yl] ethoxy}phosphonic acid;
disodium {2-[5-(1-{[(2,4-dimethyl phenyl)(6-methyl pyridin-2-yl)methyl]carbamoyl}cyclopropyl)-1H-indol-3-yl]ethoxy}phosphonic acid;
{2-[5-(1-{[(3-chlorophenyl)(2,4-dimethylphenyl)methyl] carbamoyl}cyclopropyl)-1H-indol-3-yl] ethoxy}phosphonic acid;
disodium 2-[5-(1-{[(3-chlorophenyl)(2,4-dimethylphenyl)methyl]carbamoyl}cyclopropyl)-1H-indol-3-yl] ethyl phosphate;
{2-[5-(1-{[(4-methoxy-2-methylphenyl)(phenyl)methyl] carbamoyl}cyclopropyl)-1H-indol-3-yl] ethoxy}phosphonic acid;
disodium 2-[5-(1-{[(4-methoxy-2-methylphenyl)(phenyl) methyl]carbamoyl}cyclopropyl)-1H-indol-3-yl]ethyl phosphate;
(2-{5-[1-({[4-methoxy-2-(pyrrolidin-1-yl)phenyl](phenyl)methyl}carbamoyl)cyclopropyl]-1H-indol-3-yl}ethoxy)phosphonic acid;
disodium 2-{5-[1-({[4-methoxy-2-(pyrrolidin-1-yl)phenyl](phenyl)methyl}carbamoyl)cyclopropyl]-1H-indol-3-yl}ethyl phosphate;
{2-[5-(1-{[cyclopropyl (2,4-dimethylphenyl)methyl] carbamoyl}cyclopropyl)-1H-indol-3-yl] ethoxy}phosphonic acid;
disodium 2-[5-(1-{[cyclopropyl(2,4-dimethylphenyl) methyl]carbamoyl}cyclopropyl)-1H-indol-3-yl]ethyl phosphate;
(2-{5-[1-({[4-methyl-2-(morpholin-4-yl) phenyl](phenyl) methyl}carbamoyl) cyclopropyl]-1H-indol-3-yl}ethoxy) phosphonic acid;
disodium 2-{5-[1-({[4-methyl-2-(morpholin-4-yl) phenyl](phenyl)methyl}carbamoyl) cyclopropyl]-1H-indol-3-yl}ethyl phosphate;
{2-[5-(1-{[(dimethyl-1,2-oxazol-4-yl) (phenyl)methyl] carbamoyl}cyclopropyl)-1H-indol-3-yl] ethoxy}phosphonic acid; and
disodium 2-[5-(1-{[(dimethyl-1,2-oxazol-4-yl) (phenyl) methyl]carbamoyl}cyclopropyl)-1H-indol-3-yl]ethyl phosphate.

10. A pharmaceutical composition comprising a compound according to claim 1 and a pharmaceutically acceptable excipient.

11. The pharmaceutical composition according to claim 10, wherein said composition is in a form of a suspension, a gel, an oil, a powder, an aerosol, or a spray.

12. A method of treating a respiratory disease, said respiratory disease being selected from the group consisting of neutrophilic asthma, chronic obstructive pulmonary disease (COPD), asthma-COPD overlap syndrome (ACOS), idiopathic pulmonary fibrosis (IPF), and chronic rhinosinusitis with nasal polyps (CRSwNP) comprising the administration of a pharmaceutical composition according to claim 10 to a subject in need of treatment.

13. The method according to claim 12, wherein said composition is administered by a nasal inhalation.

14. A device comprising a pharmaceutical composition according to claim 10, said device being a dry powder inhaler (DPI) or a metered dose inhaler (MDI).

* * * * *